United States Patent
Yu et al.

(10) Patent No.: US 12,359,173 B2
(45) Date of Patent: Jul. 15, 2025

(54) SERUM-FREE AND XENO-FREE CULTURE MEDIUM FOR EXPANDING MESENCHYMAL STEM CELLS

(71) Applicant: NUWACELL BIOTECHNOLOGIES CO., LTD., Anhui (CN)

(72) Inventors: Junying Yu, Anhui (CN); Hailan Li, Anhui (CN); Tao Zhou, Anhui (CN); Chen Meng, Anhui (CN); Zhenlei Gan, Anhui (CN); Yongqiang Zhao, Anhui (CN); Ying Zhang, Anhui (CN)

(73) Assignee: NUWACELL BIOTECHNOLOGIES CO., LTD., Anhui (CN)

( * ) Notice: Subject to any disclaimer, the term of this patent is extended or adjusted under 35 U.S.C. 154(b) by 18 days.

(21) Appl. No.: 18/231,518

(22) Filed: Aug. 8, 2023

(65) Prior Publication Data
US 2024/0368554 A1     Nov. 7, 2024

Related U.S. Application Data

(63) Continuation of application No. PCT/CN2023/092448, filed on May 6, 2023.

(51) Int. Cl.
    *C12N 5/0775*     (2010.01)
(52) U.S. Cl.
    CPC ........ *C12N 5/0668* (2013.01); *C12N 2500/24* (2013.01); *C12N 2500/32* (2013.01); *C12N 2500/38* (2013.01); *C12N 2500/46* (2013.01); *C12N 2500/80* (2013.01); *C12N 2500/90* (2013.01); *C12N 2500/98* (2013.01); *C12N 2500/99* (2013.01); *C12N 2501/115* (2013.01); *C12N 2501/33* (2013.01); *C12N 2501/39* (2013.01); *C12N 2501/998* (2013.01); *C12N 2501/999* (2013.01)

(58) Field of Classification Search
None
See application file for complete search history.

(56) References Cited

U.S. PATENT DOCUMENTS

| | | | |
|---|---|---|---|
| 8,835,175 B2 * | 9/2014 | Diez Cervantes ... | C12N 5/0668 435/405 |
| 2020/0246386 A1 * | 8/2020 | Ofir ........................ | A61K 35/28 |
| 2021/0115395 A1 * | 4/2021 | Raviv .................... | A61K 35/35 |

FOREIGN PATENT DOCUMENTS

| | | |
|---|---|---|
| CN | 110592007 B | 8/2020 |
| CN | 112608894 A | 4/2021 |
| CN | 112725269 A | 4/2021 |
| CN | 113403271 A | 9/2021 |
| CN | 114214274 A | 3/2022 |
| CN | 115975919 A | 4/2023 |

OTHER PUBLICATIONS

Nikolits et al., (2021) Towards physiologic culture approaches to improve standard cultivation of mesenchymal stem cells. Cells, 10(4):886 (Year: 2021).*
Formulation for Dulbecco's Modified Eagle's Medium (DMEM) ATCC® 30-2002. Datasheet [online]. ATCC, 2023 [retrieved on Jan. 13, 2024]. Retrieved from the Internet:<URL: file:///C:/Users/kjohnson3/Downloads/ATCC%20Medium%2030-2002.pdf> (Year: 2023).*
Fekete et al., (2013) Essential components for ex vivo proliferation of mesenchymal stromal cells. Tissue Engineering Part C: Methods, 20(2): 129-139 (Year: 2013).*
DMEM/F-12. Datasheet [online. Sigma, 2024 [retrieved on Jun. 1, 2024]. Retrieved from the Internet: <URL: https://www.sigmaaldrich.com/US/en/technical-documents/technical-article/cell-culture-and-cell-culture-analysis/mammalian-cell-culture/dme-f120> (Year: 2024).*
Li B-Y et al., "Large-Scale Expansion of Human Umbilical Cord Mesenchymal Stem Cells in Human Platelet Lysate as a Substitute of Fetal Bovine Serum", Chinese Journal of Tissue Engineering Research 18(10):1539-1546 (Mar. 5, 2014), together with an Abstract.
Naskou M.C. et al., "Platelet Lysate as a Novel Serum-Free Media Supplement for the Culture of Equine Bone Marrow-Derived Mesenchymal Stem Cells", Stem Cell Research & Therapy 9(75):1-13 (Mar. 2018).
Xu J. et al., "Chemical-Defined Medium Supporting the Expansion of Human Mesenchymal Stem Cells", Stem Cell Research & Therapy 11(125):1-11 (Mar. 2020).
International Search Report and Written Opinion dated Dec. 14, 2023 received from International Application No. PCT/CN2023/092448.

* cited by examiner

*Primary Examiner* — Kara D Johnson
(74) *Attorney, Agent, or Firm* — Scully, Scott, Murphy & Presser, P.C.

(57) ABSTRACT

The present disclosure described herein provides, inter alia, a serum-free and xeno-free culture medium capable of supporting the prolonged expansion of mesenchymal stem cells (MSCs) and a kit comprising the same. The present disclosure also provides a method for expanding mesenchymal stem cells (MSCs) using the culture medium as disclosed as well as a substantially homogeneous population of MSCs produced by said method.

30 Claims, 20 Drawing Sheets
(8 of 20 Drawing Sheet(s) Filed in Color)

CD90

SERUM-FREE AND XENO-FREE CULTURE MEDIUM FOR EXPANDING MESENCHYMAL STEM CELLS

CROSS REFERENCE TO RELATED APPLICATIONS

This patent application is a continuation of and claims the benefit of international patent application No. PCT/CN2023/092448, filed on May 6, 2023, the disclosure of which is incorporated herein in its entirety by reference.

TECHNICAL FIELD

The present disclosure generally relates to the field of cell culture technology, in particular to a serum-free and xeno-free culture medium for expanding mesenchymal stem cells (MSCs) and a kit comprising the same. The present disclosure also relates to a method for expanding mesenchymal stem cells (MSCs) using the culture medium or kit as disclosed, and a population of MSCs produced by the method as disclosed.

BACKGROUND

Mesenchymal stem cells (MSCs) are stem cells having multipotency and self-renewing potency. MSCs can differentiate into a variety of cells including osteoblasts, chondrocytes, and adipocytes. Furthermore, MSCs are known to have a paracrine effect and a cellular adhesive interaction by self-produced humoral factors. On the basis of these effects, MSCs exert the capability of repairing and regenerating target tissues and cells as well as the capability of controlling an immune response, for example, in anti-inflammation, thereby providing a therapeutic effect on various diseases.

MSCs can be derived from various adult or fetal tissues (e.g., bone marrow, embryonic yolk sac, placenta, umbilical cord tissues, umbilical cord blood, amniotic fluid, and adipose tissue). Notwithstanding, these cell sources are limited. Unlimited and reproducible MSCs can be produced from induced pluripotent stem cells (iPSCs).

In clinical applications, a homogeneous and robust population with a high number of cells is strongly desired. Currently, many protocols for expanding MSCs have been developed to obtain a high number of MSCs.

At present, the system for expanding MSCs is mainly based on the basal medium supplemented with fetal bovine serum (FBS). However, FBS contains heterogeneous proteins, which may carry bacteria, viruses, and protein infectious diseases. Further, some studies have shown that MSCs can engulf proteins present in the culture medium, such as bovine serum protein (7 mg-30 mg/$10^8$ cells), which can lead to the production of anti-bovine protein antibodies and cell-mediated immune responses upon repeated infusion of MSCs in patients.

Many serum-free media have been also developed to expand MSCs. However, these media could not reliably support the prolonged expansion of MSCs. For example, MSCs of high passage number not only lack proliferation potential, but also lose stem cell characteristics such as phenotype.

Thus, there remains a need to provide improved medium for expanding MSCs.

SUMMARY

The present disclosure provides, among other things, a serum-free and xeno-free culture medium, a kit comprising the same, a method for expanding mesenchymal stem cells (MSCs) using the culture medium or kit, and a population of MSCs produced by the method as disclosed.

One aspect of the present disclosure relates to a serum-free and xeno-free culture medium capable of supporting the prolonged expansion of mesenchymal stem cells (MSCs), comprising (a) a basal medium; (b) an ethanolamine-based compound; (c) a putrescine-based compound; and (d) a human platelet lysate (HPLT).

In certain embodiments, the ethanolamine-based compound is present in the culture medium at a concentration of 1 to 30 µM.

In certain embodiments, the putrescine-based compound is present in the culture medium at a concentration of 1 to 30 µM.

In certain embodiments, the human platelet lysate is present in the culture medium at a concentration of 0.1% to 20% by volume.

In certain embodiments, the ethanolamine-based compound comprises ethanolamine, and the putrescine-based compound comprises putrescine dihydrochloride.

In certain embodiments, the culture medium further comprises a transferrin.

In certain embodiments, the transferrin is present in the culture medium at a concentration of 1 to 200 µg/ml.

In certain embodiments, the culture medium further comprises an insulin-based compound. In certain embodiments, the insulin-based compound is present in the culture medium at a concentration of 1 to 15 µg/ml.

In certain embodiments, the culture medium further comprises an antioxidant. In certain embodiments, the antioxidant is present in the culture medium at a concentration of 1 µg/mL to 200 µg/mL.

In certain embodiments, the culture medium further comprises a glutamine or its derivative. In certain embodiments, the glutamine or its derivative is present in the culture medium at a concentration of 0.1% to 5% by volume.

In certain embodiments, the culture medium comprises 5 to 30 µM of ethanolamine, 1 to 20 µM of putrescine dihydrochloride, 0.1% to 10% by volume of HPLT, 1 to 150 µg/ml of transferrin, 1 to 10 µg/ml of insulin, 1 to 150 µg/ml of ascorbate, and 0.5% to 5% by volume of glutamine in the basal medium.

In certain embodiments, the culture medium further comprises a growth factor.

In certain embodiments, the growth factor is selected from the group consisting of EGF, IGF, VEGF, PDGF, FGF2, TGFβ and any combination thereof.

In certain embodiments, the growth factor is present in the culture medium at a concentration of 1 to 20 ng/ml.

In certain embodiments, the culture medium further comprises a corticoid compound.

In certain embodiments, the corticoid compound is selected from the group consisting of hydrocortisone, corticosterone, dehydrocorticosterone, cortisone, and any combination thereof.

In certain embodiments, the corticoid compound is present in the culture medium at a concentration of 0.1 to 5 µM.

In certain embodiments, the culture medium further comprises a human serum albumin (HSA).

In certain embodiments, the human serum albumin (HSA) comprises dialyzed HSA.

In certain embodiments, the human serum albumin (HSA) is present in the culture medium at a concentration of 1 to 20 mg/ml.

In certain embodiments, the culture medium further comprises a heparin-based compound.

In certain embodiments, the heparin-based compound is present in the culture medium at a concentration of 1 to 150 μg/ml.

In certain embodiments, the culture medium further comprises one or more selected from the group consisting of lipoic acid, sulfate, ferric salt, selenite, pyruvate, monothioglycerol (MTG), and nicotinamide-based compound.

In certain embodiments, the culture medium comprises 5 to 30 μM of ethanolamine, 1 to 20 μM of putrescine dihydrochloride, 0.1% to 10% by volume of HPLT, 1 to 150 μg/ml of transferrin, 1 to 10 μg/ml of insulin, 1 to 150 μg/ml of ascorbate, 0.5% to 5% by volume of glutamine, 1 to 15 ng/ml of FGF2, 0.5 to 5 μM of hydrocortisone, 1 to 10 μM of lipoic acid, 1 to 30 μM of $FeSO_4$, and 0.1 to 10 μM of $Fe(NO_3)_3$ in the basal medium.

In certain embodiments, the culture medium comprises 5 to 30 μM of ethanolamine, 1 to 20 μM of putrescine dihydrochloride, 0.1% to 10% by volume of HPLT, 1 to 150 μg/ml of transferrin, 1 to 10 μg/ml of insulin, 1 to 150 μg/ml of ascorbate, 0.5% to 5% by volume of glutamine, 1 to 15 ng/ml of FGF2, 0.5 to 5 μM of hydrocortisone, 5 to 20 ng/ml of $Na_2SeO_3$, 0.05 to 5 mg/ml of sodium pyruvate, 1 to 10 mg/ml of HSA, 10 to 150 μM of MTG, 0.5 to 20 mM of nicotinamide (NAM), and 10 to 100 μg/ml of heparin sodium in the basal medium.

Another aspect of the present disclosure relates to a kit comprising the culture medium of the present disclosure.

Further another aspect of the present disclosure relates to a method for expanding mesenchymal stem cells (MSCs), comprising contacting the MSCs with the culture medium of the present disclosure.

In certain embodiments, the MSCs are continuously expanded for multiple passages, such as at least 4, 7 and 9 passages.

Still another aspect of the present disclosure relates to a substantially homogeneous population of MSCs produced by the method of the present disclosure.

BRIEF DESCRIPTION OF THE DRAWINGS

The patent or application file contains at least one drawing executed in color. Copies of this paper or patent application publication with color drawing(s) will be provided by the Office upon request and payment of the necessary fee.

Some embodiments of this disclosure are herein described, by way of example only, with reference to the accompanying drawings. With specific reference now to the drawings in detail, it is stressed that the particulars shown are by way of example and for purposes of illustrative discussion of embodiments of this disclosure. In this regard, the description taken with the drawings makes apparent to those skilled in the art how embodiments of this disclosure may be practiced.

FIGS. 2A-2B show the different effects of M1 medium and M2 medium with different concentrations of HPLT on the expansion of iMSCs according to Example 2, wherein FIG. 2A shows the cell morphologies of expanded iMSCs, and FIG. 2B shows the cell numbers of expanded iMSCs.

FIGS. 3A-3B show the different effects of M1 medium and M2 medium on the prolonged expansion of iMSCs according to Example 3, wherein FIG. 3A shows the cell numbers of iMSCs of passages 6, 7 and 8, and FIG. 3B shows the CD90 expressions of iMSCs of passages 1, 4, 5 and 7.

FIGS. 4A-4B show the results of CFSE-based T cell proliferation assay of iMSCs expanded in M1 medium and M2 medium according to Example 4, wherein FIG. 4A shows the cell morphologies of activated T cells co-cultured with or without expanded iMSCs, and FIG. 4B shows the percentages of divided T cell population for activated T cells co-cultured with or without expanded iMSCs.

FIGS. 6A-6B shows the effect of different media, I, II, III, IV, V and M1 on the expansion of iMSCs according to Example 6, wherein FIG. 6A shows the cell morphologies of cultured iMSCs, and FIG. 6B shows the cell numbers of cultured iMSCs.

FIGS. 10A-10B show the results of the tri-lineage differentiation and the CFSE-based T cell proliferation assay of expanded iMSCs according to Example 10, wherein FIG. 10A shows the morphologies of the adipogenic (left panel), osteogenic (middle panel) and chondrogenic (right panel) cells differentiated from iMSCs expanded in M3, and FIG. 10B shows the percentages of divided T cell population for activated T cells co-cultured with or without iMSCs expanded in M1 and M3 and for un-activated T cells.

FIGS. 12A-12B show the effect of HSA and in particular dialyzed HSA in M3 on the expansion of iMSCs according to Example 12, wherein FIG. 12A shows the cell morphologies of iMSCs expanded in M3 media with dialyzed HSA or un-dialyzed HSA and without any HSA, and FIG. 12B shows the cell numbers of the above iMSCs.

FIGS. 15A-15B show the effect of different media on the cell morphology and the Population Doubling Time (PDT) of iMSCs during the prolonged expansion according to Example 15, wherein FIG. 15A shows the PDT curve of iMSCs from passage 3 to passage 9 during the prolonged expansion using M1 or M5, and FIG. 15B shows the cell morphology of iMSCs of passage 8 during the prolonged expansion using M1, M4 or M5.

17A shows the morphologies of the adipogenic (left panel), osteogenic (middle panel) and chondrogenic (right panel) cells differentiated from iMSCs expanded in M5, and FIG. 17B shows the percentages of divided T cell population for activated T cells co-cultured with or without iMSCs expanded in M1 and M5 and for un-activated T cells.

DETAILED DESCRIPTION

Figure 1:
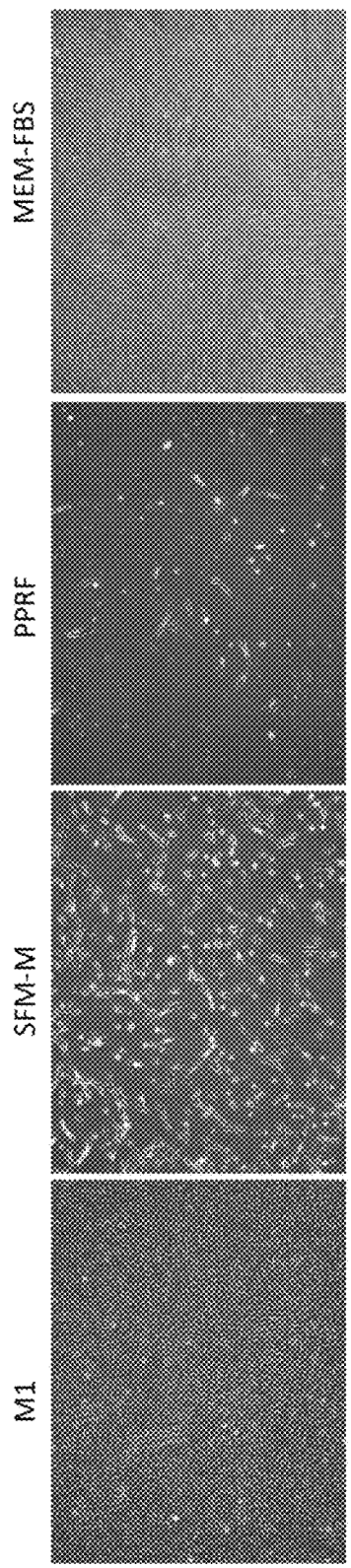
FIG. 1 shows the bright-field images of iMSCs cultured in different media, M1, SFM-M, PPRF and MEM-FBS, according to Example 1.

It is to be appreciated that certain aspects, modes, embodiments, variations and features of the present disclosure are described below in various levels of detail in order to provide a substantial understanding of the present technology.

Reference throughout this specification to "one embodiment", "another embodiment", "a preferred embodiment(s)", "some embodiments", or "a certain embodiment(s)", means that a particular feature, structure or characteristic described in connection with the embodiment(s) is included in at least one or more embodiments of the present disclosure. Also, the particular feature(s), structure(s), or characteristic(s) in one embodiment may be combined with those in one or more other embodiments in any suitable manner.

The present disclosure illustratively described herein suitably may be practiced in the absence of any element or elements, limitation or limitations that are not specifically disclosed herein. As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

Further, in each instance herein any of the terms "comprising", "consisting essentially of", and "consisting of", may be replaced with either of the other two terms.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

Unless defined otherwise, all technical and scientific terms used herein have the meaning commonly understood by a person skilled in the art to which this disclosure belongs. However, for convenience and completeness, particular terms and their meanings are set forth below and throughout the specification.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

The term "about" or "approximately" means within a statistically meaningful range of a value. Such a range can be within an order of magnitude, typically within 20%, more typically still within 10%, and even more typically within 5% of a given value or range. The allowable variation encompassed by the term "about" or "approximately" depends on the particular system under study, and can be readily appreciated by one of ordinary skill in the art. Whenever a range is recited within this application, every whole number integer within the range is also contemplated as an embodiment of the present disclosure.

As used herein, the term "substantially" or "essentially" refers to a quantity, level, value, number, frequency, percentage, dimension, size, amount, weight or length that is about or at least 90%, 91%, 92%, 93%, 94%, 95%, 96%, 97%, 98%, or 99% or higher compared to a reference quantity, level, value, number, frequency, percentage, dimension, size, amount, weight or length. In some embodiments, the terms "essentially the same" or "substantially the same" refer a range of quantity, level, value, number, frequency, percentage, dimension, size, amount, weight or length that is about the same as a reference quantity, level, value, number, frequency, percentage, dimension, size, amount, weight or length.

As used herein, the term "pluripotent stem cells" (PSCs) refers to cells derived from the inner cell mass of the embryonic blastocyst. Pluripotent stem cells can be pluripotent and give rise during development to all derivatives of the three primary germ layers: ectoderm, endoderm and mesoderm. Pluripotent stem cells can be of human origin (e.g., human PSC or hPSC). Pluripotent stems cells can be induced pluripotent stem cells (iPSCs) or embryonic stem cells (ESCs). ESCs (e.g., hESCs) and iPSCs (e.g., hiPSCs) are known in the art and can be readily obtained using conventional methods, for example, those described in the existing technologies, or commercially available products. Suitable methods for the generation of iPSCs from somatic or multipotent stem cells are well known to those of skill in the art. For example, iPSCs may be reliably generated from somatic cells by conventional reprogramming technologies.

As used herein, the term "pluripotency" or "pluripotent" refers to a cell that has the developmental potential to differentiate into cells of all three germ layers (Ectoderm, mesoderm, and endoderm). Pluripotency can be determined, at least in part, by assessing pluripotency characteristics of the cells. Pluripotency characteristics include, but are not limited to: (i) pluripotent stem cell morphology; (ii) the potential for unlimited self-renewal; (iii) expression of pluripotent stem cell markers including, but not limited to SSEA1 (mouse only), SSEA3/4, SSEA5, TRA1-60/81, TRA1-85, TRA2-54, GCTM-2, TG343, TG30, CD9, CD29, CD133/prominin, CD140a, CD56, CD73, CD90, CD105, OCT4, NANOG, SOX2, CD30 and/or CD50; (iv) ability to differentiate to all three somatic lineages (ectoderm, mesoderm and endoderm); (v) teratoma formation consisting of the three somatic lineages; and (vi) formation of embryoid bodies consisting of cells from the three somatic lineages.

As used herein the term "mesenchymal stem cells" or "MSCs" refers to stem cells possessing multipotency capable of differentiating into cells such as adipocytes, osteocytes, chondrocytes, myocytes, nerve cells, and cardiomyocytes. MSCs comprise primary MSCs and induced MSCs (also referred to as iMSCs). Examples of the primary MSCs include, for example, bone marrow-derived mesenchymal stem cells (BM-MSC), placental-derived mesenchymal stem cells (P-MSC), umbilical cord-derived mesenchymal stem cells (UC-MSC), adipose-derived mesenchymal stem cells (A-MSC), peripheral blood-derived mesenchymal stem cells (PB-MSC) and dental pulp-derived mesenchymal stem cells (DP-MSC). iMSCs can be differentiated from ESCs or iPSCs. When used in the present disclosure, the ESCs are obtained from commercially established human embryonic stem cell lines or human embryonic stem cells that have not been developed in vivo within 14 days of fertilization.

As used herein the term "expansion" or "expanding" refers to increasing the number of MSCs over the culturing period (by at least about 5%, 10%, 15%, 20%, 30%, 40%, 50%, 60%, 70%, 80%, 90%, 100% or more, e.g. by 2, 3, 4, 5, 6, 7, 8, 9, 10 fold or more).

As used herein, the term "culture medium" refers to a culture medium which can support the survival, growth, propagation, maintenance and/or differentiation of cells in an in vitro environment. A culture medium may have a basal medium and one or more supplements.

As used herein, the term "basal medium" refers to a basal component of a culture medium (e.g. differentiation culture medium, or expansion culture medium) relative to its supplement(s). Generally, the basal medium comprises about 95% to 99% by volume of the culture medium (e.g. differentiation culture medium, or expansion culture medium). A basal medium of a cell expansion culture medium acts as a source of nutrients, hormones and/or other factors helpful to propagate and/or proliferate the cells. A basal medium of a cell differentiation culture medium acts as a source of nutrients, hormones and/or other factors helpful to differentiate the cells.

As used herein, the term "supplement(s)" refers to an additive component(s) of a culture medium (e.g. differentiation culture medium, or expansion culture medium) relative to its basal medium. In the context of the present disclosure, the amounts or concentrations of all additive components or supplements in the culture medium (e.g., expansion medium) are calculated on the basis of the basal medium. All percents referred to in the description of the amount(s) or concentration(s) of the additive component(s) or supplement(s) are on a volume basis unless specified otherwise.

As used herein, the term "supplemented" refers to the addition of a supplement for a culture medium (e.g. expansion culture medium) into its basal medium. The supplement(s) may be added into a basal medium of a culture medium before or upon the use of the culture medium.

As used herein, the phrase "serum-free" refers to being devoid of a human or an animal serum. It should be noted that the function of serum in culturing protocols is to provide the cultured cells with an environment similar to that present in vivo (i.e., within the organism from which the cells are derived). However, the use of serum, which is derived from either an animal source (e.g., bovine serum) or a human source (human serum), is limited by the significant variations in serum components between the donor individuals (from which the serum is obtained) and the risk of having xeno contaminants (in case where an animal serum is used).

As used herein, the term "xeno-free" refers to being free of any product which is derived from non-human animal.

As used herein, the phrase "serum replacement (SR)" refers to a defined formulation, which substitutes the function of serum by providing pluripotent stem cells or mesenchymal stem cells with components needed for growth and viability.

As used herein, the term "prolonged expansion" refers to the continuous expansion of cells where the cells are passaged for multiple passages. In the context of this disclosure, the prolonged expansion can be used interchangeably with the continuous expansion.

The term "seeding" or "seeded" as used herein refers to the process of providing a cell culture to a bioreactor or another vessel. The cells may have been propagated previously in another bioreactor or vessel. Alternatively, the cells may have been frozen and thawed immediately prior to providing them to the bioreactor or vessel. The term refers to any number of cells, including a single cell.

As used herein, the term "passage" or "passaging" refers to splitting the cells in the culture vessel to 2 or more culture vessels, typically including addition of fresh culture medium. Passaging is typically done when the cells reach a certain confluency in culture.

As used herein, the term "in vitro" refers generally to activities that take place outside an organism.

As used herein, the term "in vivo" refers generally to activities that take place inside an organism.

1. Culture Medium

According to one aspect of the present disclosure, there is provided a serum-free and xeno-free culture medium capable of supporting the prolonged expansion of mesenchymal stem cells (MSCs), comprising (a) a basal medium; (b) an ethanolamine-based compound; (c) a putrescine-based compound; and (d) a human platelet lysate (HPLT).

According to the present disclosure, based on the synergistic effect of the combination of an ethanolamine-based compound, a putrescine-based compound and HPLT, this culture medium can significantly promote the expansion of MSCs while stably maintaining the stem cell phenotype (CD90$^+$) of the MSCs during the prolonged expansion. On the basis of this, the culture medium according to the present disclosure can support the prolonged expansion of MSCs substantially without losing MSC characteristics such as morphology, phenotype, differentiation potential and immunomodulatory effect, and thus is more suitable for large-scale production of MSC products for clinical applications.

Mesenchymal Stem Cells (MSCs)

Any MSCs may be expanded using the expansion medium of the present disclosure. Examples of MSCs comprise primary MSCs and induced MSCs (iMSCs). Examples of the primary MSCs include, for example, BM-MSC, P-MSC, UC-MSC, A-MSC, PB-MSC and DP-MSC. iMSCs can be derived (e.g., differentiated) from pluripotent stem cells. Pluripotent stems cells can comprise induced pluripotent stem cells (e.g. hiPSCs), embryonic stem cells (e.g., hESCs), naïve PSCs (NPSCs) and extended pluripotent stem cells (EPSCs). In certain embodiments, the iMSCs are ESC-derived MSCs. In certain embodiments, the iMSCs are iPSC-derived MSCs. In certain embodiments, the iMSCs are NPSC-derived MSCs. In certain embodiments, the MSCs are EPSC-derived MSCs. Commercially available MSCs can also be used in the present disclosure.

ESCs (e.g., hESCs) and iPSCs (e.g., hiPSCs) are known in the art and can be readily obtained using conventional methods, for example, those described in the existing technologies, or commercially available products. For example, CytoTune iPS 2.0 Sendai Reprogramming Kit (ThermoFisher Scientific) can be used to reliably generate induced pluripotent stem cells (iPSCs) from somatic cells, including PBMCs and T-cells.

The primary MSCs may be obtained using any method known in the art. For example, MSCs can be obtained from bone marrow using standard procedures. For example, bone marrow aspirates or biopsies can be collected from donors (e.g. healthy donors) and MSCs can be isolated therefrom. Generally, mononuclear cells are typically isolated from bone marrow aspirates by gradient centrifugation, are then seeded into flasks containing MSC medium, such as Dulbecco's modified Eagle medium (DMEM)-low glucose supplemented with 10 mM L-glutamine and 10% fetal calf serum (FCS), and grown at 37° C. under a humidified 5% $CO_2$ atmosphere. Non-adherent cells are typically removed after 24 hours (e.g. by washing with PBS-HSA solution). The culture medium is changed every 4 days and after 2 weeks the cultures should be mostly confluent. MSCs are recovered using trypsin and re-plated as passage 1 cells. Cells can be kept in culture for at least 8 passages and tested routinely for the presence of MSC-associated surface molecules.

iPSCs (e.g., hiPSCs) can be differentiated using any common method to generate iMSCs. For example, the differentiation method described in CN110592007B, which is incorporated herein by reference in its entirety, may be used to generate iMSCs from iPSCs.

MSCs may be characterized by both the presence of certain cell surface markers such as CD90 and the absence of certain cell surface markers. MSCs may also be identified by functional assays both in vitro and in vivo, particularly assays relating to the ability of stem cells to give rise to multiple differentiated progeny, assays for responsiveness to canonical WNT signaling, and the like.

Basal Medium

As implied by the name, the basal medium can support the survival, maintenance, growth, and proliferation of cells as a culture medium, and is a basal component for the expansion medium. Generally, the basal medium comprises about 95% to 99% by volume of the expansion medium. The basal medium used in the expansion medium of the present disclosure may be a common basal medium in the art.

Examples of the basal medium comprises DMEM/F12 (e.g., Gibco Cat. #C11330500BT), BME medium (e.g., Gibco Cat. #21010046, or Sigma-Aldrich Cat. #B9638), IMDM medium (e.g., Gibco Cat. #12440053; or Sigma-Aldrich Cat. #I3390), Eagle MEM medium (e.g., Minimum Essential Medium (MEM), developed by Harry Eagle, Sigma-Aldrich Cat. #M2414/M2279/M5690), α-MEM medium (e.g., Gibco Cat. #12561056; or, Sigma-Aldrich Cat. #M0894), DMEM medium (e.g., Gibco Cat. #21068028), RPMI 1640 medium (e.g., Gibco Cat. #11875093), Ham's F12 medium (e.g., Gibco Cat. #11765054), or a mixture thereof. When the culture medium comprises the mixture of two or more basal media, the relative ratios of these basal media may be arbitrary.

Ethanolamine-Based Compound

As used herein, "ethanolamine-based compound" refers to ethanolamine, its derivatives, salts thereof or mixtures thereof.

Ethanolamine (also referred to as 2-aminoethanol, monoethanolamine, ETA, or MEA) is an organic chemical compound with the formula $HOCH_2CH_2NH_2$ or $C_2H_7NO$. The molecule is bifunctional, containing both a primary amine and a primary alcohol. Ethanolamine is commonly called monoethanolamine or MEA in order to be distinguished from diethanolamine (DEA) and triethanolamine (TEA).

Examples of the derivatives of ethanolamine include, but are not limited to, substituted ethanolamines such as phosphatidylethanolamine. Examples of the salts of ethanolamine and its derivatives include, but are not limited to, ethanolamine hydrochloride, and ethanolamine hydrobromide as well as hydrochloride or hydrobromide of substituted ethanolamines.

According to certain embodiments, the ethanolamine-based compound used in the culture medium may be ethanolamine. According to certain embodiments, the ethanolamine-based compound used in the culture medium may be ethanolamine hydrochloride.

According to the present disclosure, the concentration of the ethanolamine-based compound is not particularly limited as long as it can support the prolonged expansion of MSCs. According to some embodiments, the concentration of the ethanolamine-based compound is in the range of 1 to 30 μM, e.g., 1 to 5 μM, 1 to 10 μM, 1 to 15 μM, 1 to 20 μM, 1 to 25 μM, 1 to 30 μM, 2 to 5 μM, 2 to 10 μM, 2 to 15 μM, 2 to 20 μM, 2 to 25 μM, 2 to 30 μM, 3 to 5 μM, 3 to 10 μM, 3 to 15 μM, 3 to 20 μM, 3 to 25 μM, 3 to 30 μM, 4 to 5 μM, 4 to 10 μM, 4 to 15 μM, 4 to 20 μM, 4 to 25 μM, 4 to 30 μM, 5 to 10 μM, 5 to 15 μM, 5 to 20 μM, 5 to 25 μM, or 5 to 30 μM. According to some embodiments, the concentration of the ethanolamine-based compound is 1 μM, 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM, 20 μM, 21 μM, 22 μM, 23 μM, 24 μM, 25 μM, 26 μM, 27 μM, 28 μM, 29 μM, or 30 μM. According to preferred embodiments, the concentration of the ethanolamine-based compound is 5 to 30 μM.

Putrescine-Based Compound

As used herein, "putrescine-based compound" refers to putrescine and its derivatives, salts thereof, or mixtures thereof.

Putrescine is an organic compound with the formula $(CH_2)_4(NH_2)_2$. Putrescine is commonly called 1,4-butanediamine, and produced on an industrial scale by the hydrogenation of succinonitrile.

Examples of the derivatives of putrescine include, but are not limited to, substituted putrescines such as N-acetylputrescine. Examples of the salts of putrescine and its derivatives include, but are not limited to, putrescine hydrochloride, putrescine dihydrochloride, putrescine dihydrobromide, and dihydrochloride or dihydrobromide of substituted putrescines such as N-acetylputrescine.

According to certain embodiments, the putrescine-based compound used in the culture medium may be putrescine. According to certain embodiments, the putrescine-based compound used in the culture medium may be putrescine dihydrochloride.

According to the present disclosure, the concentration of the putrescine-based compound is not particularly limited as long as it can support the prolonged expansion of MSCs. According to some embodiments, the concentration of the putrescine-based compound is in the range of 1 to 30 μM, e.g., 1 to 5 μM, 1 to 10 μM, 1 to 15 μM, 1 to 20 μM, 1 to 25 μM, 1 to 30 μM, 2 to 5 μM, 2 to 10 μM, 2 to 15 μM, 2 to 20 μM, 2 to 25 μM, 2 to 30 μM, 3 to 5 μM, 3 to 10 μM, 3 to 15 μM, 3 to 20 μM, 3 to 25 μM, 3 to 30 μM, 4 to 5 μM, 4 to 10 μM, 4 to 15 μM, 4 to 20 μM, 4 to 25 μM, 4 to 30 μM, 5 to 10 μM, 5 to 15 μM, 5 to 20 μM, 5 to 25 μM, or 5 to 30 μM. According to some embodiments, the concentration of the putrescine-based compound is 1 μM, 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM, 20 μM, 21 μM, 22 μM, 23 μM, 24 μM, 25 μM, 26 μM, 27 μM, 28 μM, 29 μM, or 30 μM. According to preferred embodiments, the concentration of the putrescine-based compound is 1 to 20 μM.

Human Platelet Lysate

Human platelet lysate (HPLT) is derived from human platelets. Human platelet lysate may be derived from healthy donor human platelets and is growth factor-rich. Human platelet lysate used according to the present disclosure is commercially available, e.g., PLTGold Human Platelet Lysate (Biological Industries, #PLTGOLD500R). However, human platelet lysate from other sources are also available and can be used in the present disclosure. In the present disclosure, human platelet lysate can substantially improve the expansion efficiency for the cells during the prolonged expansion.

According to the present disclosure, the concentration of the human platelet lysate is not particularly limited as long as it can support the prolonged expansion of MSCs. According to some embodiments, the concentration of the human platelet lysate is 0.1% to 20% by volume, e.g., 0.1% to 1% by volume, 0.1% to 2% by volume, 0.1% to 3% by volume, 0.1% to 4% by volume, 0.1% to 5% by volume, 0.1% to 10% by volume, 0.1% to 15% by volume, 0.1% to 20% by volume, 0.5% to 1% by volume, 0.5% to 2% by volume, 0.5% to 3% by volume, 0.5% to 4% by volume, 0.5% to 5% by volume, 0.5% to 10% by volume, 0.5% to 15% by volume, 0.5% to 20% by volume, 1% to 2% by volume, 1% to 3% by volume, 1% to 4% by volume, 1% to 5% by volume, 1% to 10% by volume, 1% to 15% by volume, 1% to 20% by volume, 2% to 3% by volume, 2% to 4% by volume, 2% to 5% by volume, 2% to 10% by volume, 2% to 15% by volume, 2% to 20% by volume, 3% to 4% by volume, 3% to 5% by volume, 3% to 10% by volume, 3% to 15% by volume, 3% to 20% by volume, 4% to 5% by volume, 4% to 10% by volume, 4% to 15% by volume, or 4% to 20% by volume, 5% to 6% by volume, 5% to 7% by volume, 5% to 8% by volume, 5% to 9% by volume, 5% to 10% by volume, 5% to 15% by volume, or 5% to 20% by volume. According to some embodiments, the concentration of the human platelet lysate is 0.1% by volume, 0.2% by volume, 0.3% by volume, 0.4% by volume, 0.5% by volume, 0.6% by volume, 0.7% by volume, 0.8% by volume, 0.9% by volume, 1% by volume, 2% by volume, 3% by volume, 4% by volume, 5% by volume, 6% by volume, 7% by volume, 8% by volume, 9% by volume, 10% by volume, 15% by volume, or 20% by volume. According to preferred embodiments, the concentration of the human platelet lysate is 0.1% to 10% by volume.

Additional Reagents

Depending on the requirements of the present disclosure, one or more additional reagents may be optionally added into the the culture medium before or upon use of the culture medium. Additional reagents can include, for example, transferrin, insulin-based compound, growth factor, corticoid compound, human serum albumin (HSA), heparin-based compound, glutamine or its derivative, antioxidant, lipoic acid, sulfate, ferric salt, selenite, pyruvate, monothioglycerol (MTG), and nicotinamide-based compound.

Transferrin

According to some embodiments, the culture medium further comprises a transferrin. According to some embodiments, the transferrin may be holo-transferrin, partially saturated transferrin, or recombinant transferrin.

According to the present disclosure, the concentration of the transferrin is not particularly limited as long as it can support the prolonged expansion of MSCs. According to some embodiments, the concentration of the transferrin is 1 to 200 µg/ml, e.g., 1 to 5 µg/ml, 1 to 10 µg/ml, 1 to 15 µg/ml, 1 to 20 µg/ml, 1 to 25 µg/ml, 1 to 30 µg/ml, 1 to 35 µg/ml, 1 to 40 µg/ml, 1 to 45 µg/ml, 1 to 50 µg/ml, 1 to 60 µg/ml, 1 to 70 µg/ml, 1 to 80 µg/ml, 1 to 90 µg/ml, 1 to 100 µg/ml, 1 to 110 µg/ml, 1 to 120 µg/ml, 1 to 130 µg/ml, 1 to 140 µg/ml, 1 to 150 µg/ml, 1 to 160 µg/ml, 1 to 170 µg/ml, 1 to 180 µg/ml, 1 to 190 µg/ml, 1 to 200 µg/ml, 3 to 5 µg/ml, 3 to 10 µg/ml, 3 to 15 µg/ml, 3 to 20 µg/ml, 3 to 25 µg/ml, 3 to 30 µg/ml, 3 to 35 µg/ml, 3 to 40 µg/ml, 3 to 45 µg/ml, 3 to 50 µg/ml, 3 to 60 µg/ml, 3 to 70 µg/ml, 3 to 80 µg/ml, 3 to 90 µg/ml, 3 to 100 µg/ml, 3 to 110 µg/ml, 3 to 120 µg/ml, 3 to 130 µg/ml, 3 to 140 µg/ml, 3 to 150 µg/ml, 3 to 160 µg/ml, 3 to 170 µg/ml, 3 to 180 µg/ml, 3 to 190 µg/ml, 3 to 200 µg/ml, 5 to 10 µg/ml, 5 to 15 µg/ml, 5 to 20 µg/ml, 5 to 25 µg/ml, 5 to 30 µg/ml, 5 to 35 µg/ml, 5 to 40 µg/ml, 5 to 45 µg/ml, 5 to 50 µg/ml, 5 to 60 µg/ml, 5 to 70 µg/ml, 5 to 80 µg/ml, 5 to 90 µg/ml, 5 to 100 µg/ml, 5 to 110 µg/ml, 5 to 120 µg/ml, 5 to 130 µg/ml, 5 to 140 µg/ml, 5 to 150 µg/ml, 5 to 160 µg/ml, 5 to 170 µg/ml, 5 to 180 µg/ml, 5 to 190 µg/ml, 5 to 200 µg/ml, 7 to 10 µg/ml, 7 to 15 µg/ml, 7 to 20 µg/ml, 7 to 25 µg/ml, 7 to 30 µg/ml, 7 to 35 µg/ml, 7 to 40 µg/ml, 7 to 45 µg/ml, 7 to 50 µg/ml, 7 to 60 µg/ml, 7 to 70 µg/ml, 7 to 80 µg/ml, 7 to 90 µg/ml, 7 to 100 µg/ml, 7 to 110 µg/ml, 7 to 120 µg/ml, 7 to 130 µg/ml, 7 to 140 µg/ml, 7 to 150 µg/ml, 7 to 160 µg/ml, 7 to 170 µg/ml, 7 to 180 µg/ml, 7 to 190 µg/ml, 7 to 200 µg/ml. 9 to 10 µg/ml, 9 to 15 µg/ml, 9 to 20 µg/ml, 9 to 25 µg/ml, 9 to 30 µg/ml, 9 to 35 µg/ml, 9 to 40 µg/ml, 9 to 45 µg/ml, 9 to 50 µg/ml, 9 to 60 µg/ml, 9 to 70 µg/ml, 9 to 80 µg/ml, 9 to 90 µg/ml, 9 to 100 µg/ml, 9 to 110 µg/ml, 9 to 120 µg/ml, 9 to 130 µg/ml, 9 to 140 µg/ml, 9 to 150 µg/ml, 9 to 160 µg/ml, 9 to 170 µg/ml, 9 to 180 µg/ml, 9 to 190 µg/ml or 9 to 200 µg/ml. According to some embodiments, the concentration of the transferrin is 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 15 µg/ml, 20 µg/ml, 25 µg/ml, 30 µg/ml, 35 µg/ml, 40 µg/ml, 45 µg/ml, 50 µg/ml, 60 µg/ml, 70 µg/ml, 80 µg/ml, 90 µg/ml, 100 µg/ml, 110 µg/ml, 120 µg/ml, 130 µg/ml, 140 µg/ml, 150 µg/ml, 160 µg/ml, 170 µg/ml, 180 µg/ml, 190 µg/ml or 200 µg/ml. According to preferred embodiments, the concentration of the transferrin is 1 to 150 µg/m.

Insulin-Based Compound

As used herein, "insulin-based compound" refers to insulin, its analogs or derivatives thereof, or mixtures thereof.

According to some embodiments, the insulin-based compound comprises an insulin. According to some embodiments, the insulin-based compound may be analogs or derivatives of insulin such as Insulin Lispro, Insulin aspart, and Insulin glulisine.

According to the present disclosure, the concentration of the insulin-based compound is not particularly limited as long as it can support the prolonged expansion of MSCs. According to some embodiments, the concentration of the insulin-based compound is 1 to 15 µg/ml, e.g., 1 to 5 µg/ml, 1 to 10 µg/ml, 1 to 15 µg/ml, 2 to 5 µg/ml, 2 to 10 µg/ml, 2 to 15 µg/ml, 3 to 5 µg/ml, 3 to 10 µg/ml, 3 to 15 µg/ml, 4 to 5 µg/ml, 4 to 10 µg/m, 4 to 15 µg/ml, 5 to 10 µg/ml, 5 to 15 µg/m, 6 to 10 µg/ml, 6 to 15 µg/m, 7 to 10 µg/ml, 7 to 15 µg/m, 8 to 10 µg/ml, 8 to 15 µg/m, 9 to 10 µg/ml, 9 to 15 µg/m, or 10 to 15 µg/ml. According to some embodiments, the concentration of the insulin-based compound is 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 11 µg/ml, 12 µg/ml, 13 µg/ml, 14 µg/ml or 15 µg/ml. According to preferred embodiments, the concentration of the insulin-based compound is 1 to 10 µg/ml.

Glutamine or its Derivative

According to some embodiments, the culture medium further comprises glutamine or its derivative.

According to some embodiments, glutamine or its derivative may be a glutamine such as L-glutamine or substituted glutamine such as an alanyl-glutamine. Alanyl-glutamine is a chemical compound which in the form L-alanyl-L-glutamine is used in dietary supplementation, in parenteral nutrition, and in cell culture. L-Alanyl-L-glutamine is sold under the name GlutaMAX by Thermo Fisher Scientific.

According to the present disclosure, the concentration of the glutamine or its derivative is not particularly limited as long as it can support the prolonged expansion of MSCs.

According to some embodiments, the concentration of the glutamine or its derivative is 0.1% to 5% by volume, e.g., 0.1% to 1% by volume, 0.1% to 2% by volume, 0.1% to 3% by volume, 0.1% to 4% by volume, 0.1% to 5% by volume, 0.2% to 1% by volume, 0.2% to 2% by volume, 0.2% to 3% by volume, 0.2% to 4% by volume, 0.2% to 5% by volume, 0.3% to 1% by volume, 0.3% to 2% by volume, 0.3% to 3% by volume, 0.3% to 4% by volume, 0.3% to 5% by volume, 0.4% to 1% by volume, 0.4% to 2% by volume, 0.4% to 3% by volume, 0.4% to 4% by volume, 0.4% to 5% by volume, 0.5% to 1% by volume, 0.5% to 2% by volume, 0.5% to 3% by volume, 0.5% to 4% by volume or 0.5% to 5% by volume. According to some embodiments, the concentration of the glutamine or its derivative is 0.1% by volume, 0.2% by volume, 0.3% by volume, 0.4% by volume, 0.5% by volume, 0.6% by volume, 0.7% by volume, 0.8% by volume, 0.9% by volume, 1% by volume, 2% by volume, 3% by volume, 4% by volume, or 5% by volume. According to preferred embodiments, the concentration of the glutamine or its derivative is 0.5% to 5% by volume.

Antioxidant

According to some embodiments, the culture medium further comprises an antioxidant.

As used herein, "antioxidant" refers to a compound that inhibits oxidation (usually occurring as autoxidation) in a cell, a chemical reaction that can produce free radicals. The antioxidant may be an ascorbic acid, an analog thereof, a derivative thereof, or a salt thereof.

Antioxidant comprises ascorbic acid, ascorbate such as magnesium salt such as L(+)-Ascorbic acid magnesium salt, sodium salt such as L(+)-Ascorbic acid sodium salt, and analogs or derivatives such as for example, Ascorbyl Glucoside, 3-ethylascorbic acid, Ascorbyl Tetraisopalmitate, Ascorbic acid phosphate salt, and ascorbyl palmitate.

According to some embodiments, the antioxidant is ascorbate. According to some embodiments, the antioxidant is Na Ascorbate or Mg Ascorbate.

According to the present disclosure, the concentration of the antioxidant is not particularly limited as long as it can support the prolonged expansion of MSCs. According to some embodiments, the concentration of the antioxidant is 1 to 200 µg/ml, e.g., 1 to 5 µg/ml, 1 to 10 µg/ml, 1 to 15 µg/ml, 1 to 20 µg/ml, 1 to 25 µg/ml, 1 to 30 µg/ml, 1 to 35 µg/ml, 1 to 40 µg/ml, 1 to 45 µg/ml, 1 to 50 µg/ml, 1 to 60 µg/ml, 1 to 70 µg/ml, 1 to 80 µg/ml, 1 to 90 µg/ml, 1 to 100 µg/ml, 1 to 150 µg/ml, 1 to 200 µg/ml, 2 to 5 µg/ml, 2 to 10 µg/ml, 2 to 15 µg/ml, 2 to 20 µg/ml, 2 to 25 µg/ml, 2 to 30 µg/ml, 2 to 35 µg/ml, 2 to 40 µg/ml, 2 to 45 µg/ml, 2 to 50 µg/ml, 2 to 60 µg/ml, 2 to 70 µg/ml, 2 to 80 µg/ml, 2 to 90 µg/ml, 2 to 100 µg/ml, 2 to 150 µg/ml, 2 to 200 µg/ml, 3 to 5 µg/ml, 3 to 10 µg/ml, 3 to 15 µg/ml, 3 to 20 µg/ml, 3 to 25 µg/ml, 3 to 30 µg/ml, 3 to 35 µg/ml, 3 to 40 µg/ml, 3 to 45 µg/ml, 3 to 50 µg/ml, 3 to 60 µg/ml, 3 to 70 µg/ml, 3 to 80 µg/ml, 3 to 90 µg/ml, 3 to 100 µg/ml, 3 to 150 µg/ml, 3 to 200 µg/ml, 4 to 5 µg/ml, 4 to 10 µg/ml, 4 to 15 µg/ml, 4 to 20 µg/ml, 4 to 25 µg/ml, 4 to 30 µg/ml, 4 to 35 µg/ml, 4 to 40 µg/ml, 4 to 45 µg/ml, 4 to 50 µg/ml, 4 to 60 µg/ml, 4 to 70 µg/ml, 4 to 80 µg/ml, 4 to 90 µg/ml, 4 to 100 µg/ml, 4 to 150 µg/ml, 4 to 200 µg/ml, 5 to 10 µg/ml, 5 to 15 µg/ml, 5 to 20 µg/ml, 5 to 25 µg/ml, 5 to 30 µg/ml, 5 to 35 µg/ml, 5 to 40 µg/ml, 5 to 45 µg/ml, 5 to 50 µg/ml, 5 to 60 µg/ml, 5 to 70 µg/ml, 5 to 80 µg/ml, 5 to 90 µg/ml, 5 to 100 µg/ml, 5 to 150 µg/ml, or 5 to 200 µg/ml. According to some embodiments, the concentration of the antioxidant is 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 15 µg/ml, 20 µg/ml, 25 µg/ml, 30 µg/ml, 35 µg/ml, 40 µg/ml, 45 µg/ml, 50 µg/ml, 60 µg/ml, 70 µg/ml, 80 µg/ml, 90 µg/ml, 100 µg/ml, 110 µg/ml, 120 µg/ml, 130 µg/ml, 140 µg/ml, 150 µg/ml or 200 µg/ml. According to preferred embodiments, the concentration of the antioxidant is 1 to 150 µg/ml.

Growth Factor

According to some embodiments, the culture medium further comprises a growth factor.

Growth factors are molecules capable of stimulating a variety of cellular processes, including, for example, cell proliferation, cell migration, differentiation, and multicellular morphogenesis during development and tissue healing. Examples of growth factors include, without limitation, Bone Morphogenetic Factors (BMPs), Epidermal Growth Factors (EGFs), Endothelial Cell Growth Factors (ECGFs), Fibroblast Growth Factors (FGFs), Insulin-like Growth Factors (IGFs), Nerve Growth Factors (NGFs), Platelet-derived Growth Factors (PDGFs), transforming growth factor beta (TGFβ), and Vascular Endothelial Growth Factors (VEGFs). In the present disclosure, the addition of one or more growth factors can obviously promote the MSC expansion.

According to some embodiments, the growth factor is selected from the group consisting of EGF, IGF, VEGF, PDGF, FGF2, TGFβ and any combination thereof. According to preferred embodiments, the growth factor is FGF2, PDGF and/or TGFβ. According to more preferred embodiments, the growth factor is FGF2 and/or PDGF. According to the most preferred embodiment, the growth factor is FGF2.

Epidermal growth factor (EGF) refers to any polypeptide of the epidermal growth factor (EGF) family of proteins, or variant thereof, that stimulates cell growth and differentiation. Typically EGF exerts its activity by binding to the epidermal growth factor receptor. Accordingly, any variant of the EGF molecules that maintains their biological activity, for example, C-terminal truncated molecules, or molecules truncated at the N-terminal may be used in line with the present disclosure.

The EGF used in the culture medium of some embodiments of this disclosure can be a purified, a synthetic or a recombinantly expressed EGF protein. EGF can be obtained from various commercial sources.

Insulin-like growth factors (IGFs) are proteins with high sequence similarity to insulin. IGFs are part of a complex system that cells use to communicate with their physiologic environment. Insulin-like growth factor 1 (commonly referred to as IGF-1, at times IGF-I) is mainly secreted by the liver as a result of stimulation by growth hormone (GH). IGF-1 is important for both the regulation of normal physiology, as well as a number of pathological states, including cancer. Insulin-like growth factor 2 (IGF-2, at times IGF-II) is thought to be a primary growth factor required for early development while IGF-1 expression is required for achieving maximal growth.

The IGF used in the culture medium of some embodiments of this disclosure can be a purified, a synthetic or a recombinantly expressed IGF protein. IGF can be obtained from various commercial sources.

Vascular endothelial growth factor (VEGF) is a signaling protein produced by many cells that stimulate the formation of blood vessels. VEGFs are important signaling proteins involved in both vasculogenesis (the de novo formation of the embryonic circulatory system) and angiogenesis (the growth of blood vessels from pre-existing vasculature).

The VEGF used in the culture medium of some embodiments of this disclosure can be a purified, a synthetic or a recombinantly expressed VEGF protein. VEGF can be obtained from various commercial sources.

Platelet-derived growth factor (PDGF) refers to any of four different isoforms of PDGF that activate cellular responses through two different receptors. Those isoforms include A (observed as a homodimer designated PDGF-AA and as part of a heterodimer with the B isoform designated PDGF-AB), B (observed as a homodimer designated PDGF-BB and as part of a heterodimer with the A isoform designated PDGF-AB), C (observed as a homodimer designated PDGF-CC) and D (observed as a homodimer designated PDGF-DD). Thus, the term "PDGF" as used herein refers generally to the known PDGF homo- and heterodimers (e.g., PDGF-AA, PDGF-BB, PDGF-AB, PDGF-CC, and PDGF-DD).

According to some embodiments, PDGF used in the culture medium of some embodiments of this disclosure is PDGF-BB.

The PDGF used in the culture medium of some embodiments of this disclosure can be a purified, a synthetic or a recombinantly expressed PDGF protein. PDGF can be obtained from various commercial sources.

FGF2, also generally known as basic fibroblast growth factor (FGF basic, bFGF or FGF-β), is a member of the fibroblast growth factor family. The FGF2 used in the culture medium of some embodiments of this disclosure can be a purified, a synthetic or a recombinantly expressed FGF2 protein.

Transforming growth factor beta (TGFβ) refers to any isoform of the transforming growth factor beta (β), which functions through the same receptor signaling system in the control of proliferation, differentiation, and other functions in many cell types. TGFβ acts in inducing transformation and also acts as a negative autocrine growth factor.

According to some embodiments of this disclosure, the TGFβ comprises TGFβ1, TGFβ2 and/or TGFβ3.

Transforming growth factor beta-1 (TGFβ1) is a polypeptide member of the transforming growth factor beta superfamily of cytokines. The TGFβ1 used in the culture medium of some embodiments of this disclosure can be a purified, a synthetic or a recombinantly expressed TGFβ1 protein. TGFβ1 can be obtained from various commercial sources.

Transforming growth factor beta-2 (TGFβ2) is a polypeptide member of the transforming growth factor beta superfamily of cytokines. TGFβ2 has a vital role during embryonic development. The TGFβ2 used in the culture medium of some embodiments of this disclosure can be a purified, a synthetic or a recombinantly expressed TGFβ2 protein. TGFβ2 can be obtained from various commercial sources.

Transforming growth factor beta-3 (TGFβ3) is a polypeptide member of the transforming growth factor beta superfamily of cytokines. The TGFβ3 used in the culture medium of some embodiments of this disclosure can be a purified, a synthetic or a recombinantly expressed TGFβ3 protein. TGFβ3 can be obtained from various commercial sources.

According to the present disclosure, the concentration of the growth factor is not particularly limited as long as it can support the prolonged expansion of MSCs. According to some embodiments, the concentration of the growth factor is 1 to 20 ng/ml, e.g., 1 to 5 ng/ml, 1 to 10 ng/ml, 1 to 15 ng/ml, 1 to 20 ng/ml, 2 to 5 ng/ml, 2 to 10 ng/ml, 2 to 15 ng/ml, 2 to 20 ng/ml, 3 to 5 ng/ml, 3 to 10 ng/ml, 3 to 15 ng/ml, 3 to 20 ng/ml, 4 to 5 ng/ml, 4 to 10 ng/ml, 4 to 15 ng/ml, 4 to 20 ng/ml, 5 to 10 ng/ml, 5 to 15 ng/ml or 5 to 20 ng/ml. According to some embodiments, the concentration of the growth factor is 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml or 20 ng/ml. According to preferred embodiments, the concentration of the growth factor is 1 to 15 ng/ml.

Corticoid Compound

According to some embodiments, the culture medium further comprises a corticoid compound.

Corticoids (also known as corticosteroids) are a class of steroid hormones that are produced in the adrenal cortex of vertebrates, as well as the synthetic analogues of these hormones. Two main classes of corticosteroids, glucocorticoids and mineralocorticoids, are involved in a wide range of physiological processes, including stress response, immune response, and regulation of inflammation, carbohydrate metabolism, protein catabolism, blood electrolyte levels, and behavior. In the present disclosure, the corticoid compound can promote the MSC proliferation.

According to some embodiments, the corticoid compound is selected from the group consisting of hydrocortisone, corticosterone, dehydrocorticosterone, cortisone, and any combination thereof. According to preferred embodiments, the corticoid compound is hydrocortisone.

According to the present disclosure, the concentration of the corticoid compound is not particularly limited as long as it can support the prolonged expansion of MSCs. According to some embodiments, the concentration of the corticoid compound is 0.1 to 5 µM, e.g., 0.1 to 0.5 µM, 0.1 to 1 µM, 0.1 to 1.5 µM, 0.1 to 2 µM, 0.1 to 2.5 µM, 0.1 to 3 µM, 0.1 to 3.5 µM, 0.1 to 4 µM, 0.1 to 4.5 µM, 0.1 to 5 µM, 0.2 to 0.5 µM, 0.2 to 1 µM, 0.2 to 1.5 µM, 0.2 to 2 µM, 0.2 to 2.5 µM, 0.2 to 3 µM, 0.2 to 3.5 µM, 0.2 to 4 µM, 0.2 to 4.5 µM, 0.2 to 5 µM, 0.3 to 0.5 µM, 0.3 to 1 µM, 0.3 to 1.5 µM, 0.3 to 2 µM, 0.3 to 2.5 µM, 0.3 to 3 µM, 0.3 to 3.5 µM, 0.3 to 4 µM, 0.3 to 4.5 µM, 0.3 to 5 µM, 0.4 to 0.5 µM, 0.4 to 1 µM, 0.4 to 1.5 µM, 0.4 to 2 µM, 0.4 to 2.5 µM, 0.4 to 3 µM, 0.4 to 3.5 µM, 0.4 to 4 µM, 0.4 to 4.5 µM, 0.4 to 5 µM, 0.5 to 1 µM, 0.5 to 1.5 µM, 0.5 to 2 µM, 0.5 to 2.5 µM, 0.5 to 3 µM, 0.5 to 3.5 µM, 0.5 to 4 µM, 0.5 to 4.5 µM or 0.5 to 5 µM. According to some embodiments, the concentration of the corticoid compound is 0.1 µM, 0.2 µM, 0.3 µM, 0.4 µM, 0.5 µM, 0.6 µM, 0.7 µM, 0.8 µM, 0.9 µM, 1 µM, 1.5 µM, 2 µM, 2.5 µM, 3 µM, 3.5 µM, 4 µM, 4.5 µM or 5 µM. According to preferred embodiments, the concentration of the corticoid compound is 0.5 to 5 µM.

Human Serum Albumin (HSA)

According to some embodiments, the culture medium further comprises a human serum albumin (HSA). Human serum albumin is the serum albumin found in human blood. It is the most abundant protein in human blood plasma and constitutes about half of serum protein. In the present disclosure, HSA can promote MSC expansion.

The HSA may comprise dialyzed HSA or un-dialyzed HSA. According to preferred embodiments, the human serum albumin (HSA) is dialyzed HSA. As compared with un-dialyzed HSA, the dialyzed HSA can further promote MSC expansion and significantly lower the required HPLT concentration in promoting MSC expansion.

Dialyzed HSA may be prepared from HSA by dialysis. In detail, HSA is placed into a dialysis bag and the dialysis bag is placed in DPBS solution at 4° C. overnight to carry out the dialysis, the ratio of HSA to DPBS is 1:50 (v:v) and the pore size of the bags is 15 KD.

According to the present disclosure, the concentration of the human serum albumin is not particularly limited as long as it can support the prolonged expansion of MSCs. According to some embodiments, the concentration of the human serum albumin is 1 to 20 mg/ml, e.g., 1 to 5 mg/ml, 1 to 10 mg/ml, 1 to 15 mg/ml, 1 to 20 mg/ml, 2 to 5 mg/ml, 2 to 10 mg/ml, 2 to 15 mg/ml, 2 to 20 mg/ml, 3 to 5 mg/ml, 3 to 10 mg/ml, 3 to 15 mg/ml, 3 to 20 mg/ml, 4 to 5 mg/ml, 4 to 10 mg/ml, 4 to 15 mg/ml, 4 to 20 mg/ml, 5 to 10 mg/ml, 5 to 15 mg/ml, or 5 to 20 mg/ml. According to some embodiments, the concentration of the human serum albumin is 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml or 20 mg/ml. According to preferred embodiments, the concentration of the human serum albumin is 1 to 10 mg/ml.

Heparin-Based Compound

According to some embodiments, the culture medium further comprises a heparin-based compound.

As used herein, "heparin-based compound" refers to heparin, derivatives thereof, salts thereof, or mixtures thereof.

Heparin, a highly sulfated glycosaminoglycan variant produced and stored primarily by mast cells, is understood to possess the highest net negative charge density of all known biological molecules. Its negative charge binds to positively charged heparin-binding domains present in a large number of extracellular proteins. Such proteins include, for example, fibroblast growth factors (FGFs), vascular endothelial growth factors (VEGFs), bone morphogenetic proteins (BMPs), and large extracellular structural molecules such as fibronectin and laminin.

Examples of the derivative of heparin include, without limitation, substituted heparin. Examples of the salt of heparin or a derivative thereof include, without limitation, heparin sodium salt and heparin lithium salt, and the salts of substituted heparin.

In the present disclosure, the heparin-based compound can further promote MSC expansion.

According to preferred embodiments, the heparin-based compound is heparin sodium.

According to the present disclosure, the concentration of the heparin-based compound is not particularly limited as long as it can support the prolonged expansion of MSCs. According to some embodiments, the concentration of the heparin-based compound is 1 to 150 µg/ml, e.g., 1 to 5 µg/ml, 1 to 10 µg/ml, 1 to 15 µg/ml, 1 to 20 µg/ml, 1 to 25 µg/ml, 1 to 30 µg/ml, 1 to 35 µg/ml, 1 to 40 µg/ml, 1 to 45 µg/ml, 1 to 50 µg/ml, 1 to 60 µg/ml, 1 to 70 µg/ml, 1 to 80 µg/ml, 1 to 90 µg/ml, 1 to 100 µg/ml, 1 to 110 µg/ml, 1 to 120 µg/ml, 1 to 130 µg/ml, 1 to 140 µg/ml, 1 to 150 µg/ml, 2 to 5 µg/ml, 2 to 10 µg/ml, 2 to 15 µg/ml, 2 to 20 µg/ml, 2 to 25 µg/ml, 2 to 30 µg/ml, 2 to 35 µg/ml, 2 to 40 µg/ml, 2 to 45 µg/ml, 2 to 50 µg/ml, 2 to 60 µg/ml, 2 to 70 µg/ml, 2 to 80 µg/ml, 2 to 90 µg/ml, 2 to 100 µg/ml, 2 to 110 µg/ml, 2 to 120 µg/ml, 2 to 130 µg/ml, 2 to 140 µg/ml, 2 to 150 µg/ml, 3 to 5 µg/ml, 3 to 10 µg/ml, 3 to 15 µg/ml, 3 to 20 µg/ml, 3 to 25 µg/ml, 3 to 30 µg/ml, 3 to 35 µg/ml, 3 to 40 µg/ml, 3 to 45 µg/ml, 3 to 50 µg/ml, 3 to 60 µg/ml, 3 to 70 µg/ml, 3 to 80 µg/ml, 3 to 90 µg/ml, 3 to 100 µg/ml, 3 to 110 µg/ml, 3 to 120 µg/ml, 3 to 130 µg/ml, 3 to 140 µg/ml, 3 to 150 µg/ml, 4 to 5 µg/ml, 4 to 10 µg/ml, 4 to 15 µg/ml, 4 to 20 µg/ml, 4 to 25 µg/ml, 4 to 30 µg/ml, 4 to 35 µg/ml, 4 to 40 µg/ml, 4 to 45 µg/ml, 4 to 50 µg/ml, 4 to 60 µg/ml, 4 to 70 µg/ml, 4 to 80 µg/ml, 4 to 90 µg/ml, 4 to 100 µg/ml, 4 to 110 µg/ml, 4 to 120 µg/ml, 4 to 130 µg/ml, 4 to 140 µg/ml, 4 to 150 µg/ml, 5 to 10 µg/ml, 5 to 15 µg/ml, 5 to 20 µg/ml, 5 to 25 µg/ml, 5 to 30 µg/ml, 5 to 35 µg/ml, 5 to 40 µg/ml, 5 to 45 µg/ml, 5 to 50 µg/ml, 5 to 60 µg/ml, 5 to 70 µg/ml, 5 to 80 µg/ml, 5 to 90 µg/ml, 5 to 100 µg/ml, 5 to 110 µg/ml, 5 to 120 µg/ml, 5 to 130 µg/ml, 5 to 140 µg/ml, 5 to 150 µg/ml, 10 to 15 µg/ml, 10 to 20 µg/ml, 10 to 25 µg/ml, 10 to 30 µg/ml, 10 to 35 µg/ml, 10 to 40 µg/ml, 10 to 45 µg/ml, 10 to 50 µg/ml, 10 to 60 µg/ml, 10 to 70 µg/ml, 10 to 80 µg/ml, 10 to 90 µg/ml, 10 to 100 µg/ml, 10 to 110 µg/ml, 10 to 120 µg/ml, 10 to 130 µg/ml, 10 to 140 µg/ml or 10 to 150 µg/ml. According to some embodiments, the concentration of the heparin-based compound is 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 15 µg/ml, 20 µg/ml, 25 µg/ml, 30 µg/ml, 35 µg/ml, 40 µg/ml, 45 µg/ml, 50 µg/ml, 60 µg/ml, 70 µg/ml, 80 µg/ml, 90 µg/ml, 100 µg/ml, 110 µg/ml, 120 µg/ml, 130 µg/ml, 140 µg/ml or 150 µg/ml. According to preferred embodiments, the concentration of the heparin-based compound is 10 to 100 µg/ml.

In certain embodiments, the culture medium further comprises one or more selected from the group consisting of lipoic acid, sulfate, ferric salt, selenite, pyruvate, monothioglycerol (MTG), and nicotinamide-based compound.

Lipoic Acid

According to some embodiments, the culture medium further comprises a lipoic acid.

According to the present disclosure, the concentration of lipoic acid is not particularly limited as long as it can support the prolonged expansion of MSCs. According to some embodiments, the concentration of the lipoic acid is 1 to 20 µM, e.g., 1 to 5 µM, 1 to 10 µM, 1 to 15 µM, 1 to 20 µM, 2 to 5 µM, 2 to 10 µM, 2 to 15 µM, 2 to 20 µM, 3 to 5 µM, 3 to 10 µM, 3 to 15 µM, 3 to 20 µM, 4 to 5 µM, 4 to 10 µM, 4 to 15 µM, 4 to 20 µM, 5 to 10 µM, 5 to 15 µM, or 5 to 20 µM. According to some embodiments, the concentration of lipoic acid is 1 µM, 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM or 20 µM. According to preferred embodiments, the concentration of lipoic acid is 1 to 10 µM.

Sulfate

According to some embodiments, the culture medium further comprises a sulfate. Examples of the sulfate comprise $FeSO_4$, $MgSO_4$, $CuSO_4$ and $ZnSO_4$. According to preferred embodiments, the sulfate is $FeSO_4$.

According to the present disclosure, the concentration of the sulfate is not particularly limited as long as it can support the prolonged expansion of MSCs. According to some embodiments, the concentration of the sulfate is 1 to 50 µM, e.g., 1 to 5 µM, 1 to 10 µM, 1 to 15 µM, 1 to 20 µM, 1 to 25 µM, 1 to 30 µM, 1 to 35 µM, 1 to 40 µM, 1 to 45 µM, 1 to 50 µM, 2 to 5 µM, 2 to 10 µM, 2 to 15 µM, 2 to 20 µM, 2 to 25 µM, 2 to 30 µM, 2 to 35 µM, 2 to 40 µM, 2 to 45 µM, 2 to 50 µM, 3 to 5 µM, 3 to 10 µM, 3 to 15 µM, 3 to 20 µM, 3 to 25 µM, 3 to 30 µM, 3 to 35 µM, 3 to 40 µM, 3 to 45 µM, 3 to 50 µM, 4 to 5 µM, 4 to 10 µM, 4 to 15 µM, 4 to 20 µM, 4 to 25 µM, 4 to 30 µM, 4 to 35 µM, 4 to 40 µM, 4 to 45 µM, 4 to 50 µM, 5 to 10 µM, 5 to 15 µM, 5 to 20 µM, 5 to 25 µM, 5 to 30 µM, 5 to 35 µM, 5 to 40 µM, 5 to 45 µM or 5 to 50 µM. According to some embodiments, the concentration of the sulfate is 1 µM, 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, 20 µM, 25 µM, 30 µM, 35 µM, 40 µM, 45 µM or 50 µM. According to preferred embodiments, the concentration of the sulfate is 1 to 30 µM.

Ferric Salt

According to some embodiments, the culture medium further comprises a ferric salt. Examples of the ferric salt comprise $Fe(NO_3)_3$, $FeCl_3$, and ferric citrate. According to preferred embodiments, the ferric salt is $Fe(NO_3)_3$.

According to the present disclosure, the concentration of the ferric salt is not particularly limited as long as it can support the prolonged expansion of MSCs. According to some embodiments, the concentration of the ferric salt is 0.1 to 20 μM, e.g., 0.1 to 5 μM, 0.1 to 10 μM, 0.1 to 15 μM, 0.1 to 20 μM, 0.2 to 5 μM, 0.2 to 10 μM, 0.2 to 15 μM, 0.2 to 20 μM, 0.3 to 5 μM, 0.3 to 10 μM, 0.3 to 15 μM, 0.3 to 20 μM, 0.4 to 5 μM, 0.4 to 10 μM, 0.4 to 15 μM, 0.4 to 20 μM, 0.5 to 5 μM, 0.5 to 10 μM, 0.5 to 15 μM, 5 to 20 μM, 0.6 to 5 μM, 0.6 to 10 μM, 0.6 to 15 μM, 0.6 to 20 μM, 0.7 to 5 μM, 0.7 to 10 μM, 0.7 to 15 μM, 0.7 to 20 μM, 0.8 to 5 μM, 0.8 to 10 μM, 0.8 to 15 μM, 0.8 to 20 μM, 0.9 to 5 μM, 0.9 to 10 μM, 0.9 to 15 μM, 0.9 to 20 μM, 1 to 5 μM, 1 to 10 μM, 1 to 15 μM, 1 to 20 μM, 2 to 5 μM, 2 to 10 μM, 2 to 15 μM, 2 to 20 μM, 3 to 5 μM, 3 to 10 μM, 3 to 15 μM, 3 to 20 μM, 4 to 5 μM, 4 to 10 μM, 4 to 15 μM, 4 to 20 μM, 5 to 10 μM, 5 to 15 μM, or 5 to 20 μM. According to some embodiments, the concentration of the ferric salt is 0.1 μM, 0.2 μM, 0.3 μM, 0.4 μM, 0.5 μM, 0.6 μM, 0.7 μM, 0.8 μM, 0.9 μM, 1 μM, 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM or 20 μM. According to preferred embodiments, the concentration of the ferric salt is 0.1 to 10 μM.

Selenite

According to some embodiments, the culture medium further comprises a selenite. Examples of the selenite comprise $Na_2SeO_3$ and $K_2SeO_3$. According to preferred embodiments, the selenite is $Na_2SeO_3$.

According to the present disclosure, the concentration of the selenite is not particularly limited as long as it can support the prolonged expansion of MSCs. According to some embodiments, the concentration of the selenite is 1 to 30 ng/ml, e.g., 1 to 5 ng/ml, 1 to 10 ng/ml, 1 to 15 ng/ml, 1 to 20 ng/ml, 1 to 25 ng/ml, 1 to 30 ng/ml, 2 to 5 ng/ml, 2 to 10 ng/ml, 2 to 15 ng/ml, 2 to 20 ng/ml, 2 to 25 ng/ml, 2 to 30 ng/ml, 3 to 5 ng/ml, 3 to 10 ng/ml, 3 to 15 ng/ml, 3 to 20 ng/ml, 3 to 25 ng/ml, 3 to 30 ng/ml, 4 to 5 ng/ml, 4 to 10 ng/ml, 4 to 15 ng/ml, 4 to 20 ng/ml, 4 to 25 ng/ml, 4 to 30 ng/ml, 5 to 10 ng/ml, 5 to 15 ng/ml, 5 to 20 ng/ml, 5 to 25 ng/ml, or 5 to 30 ng/ml. According to some embodiments, the concentration of the selenite is 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 21 ng/ml, 22 ng/ml, 23 ng/ml, 24 ng/ml, 25 ng/ml, 26 ng/ml, 27 ng/ml, 28 ng/ml, 29 ng/ml, or 30 ng/ml. According to preferred embodiments, the concentration of the selenite is 5 to 20 ng/ml.

Pyruvate

According to some embodiments, the culture medium further comprises a pyruvate. Examples of pyruvate comprise sodium pyruvate and potassium pyruvate. According to preferred embodiments, the pyruvate is sodium pyruvate.

According to the present disclosure, the concentration of the pyruvate is not particularly limited as long as it can support the prolonged expansion of MSCs. According to some embodiments, the concentration of the pyruvate is 0.01 to 10 mg/ml, e.g., 0.01 to 1 mg/ml, 0.01 to 2 mg/ml, 0.01 to 3 mg/ml, 0.01 to 4 mg/ml, 0.01 to 5 mg/ml, 0.01 to 7.5 mg/ml, 0.01 to 10 mg/ml, 0.02 to 1 mg/ml, 0.02 to 2 mg/ml, 0.02 to 3 mg/ml, 0.03 to 1 mg/ml, 0.03 to 2 mg/ml, 0.03 to 3 mg/ml, 0.03 to 4 mg/ml, 0.03 to 5 mg/ml, 0.03 to 7.5 mg/ml, 0.03 to 10 mg/ml, 0.05 to 1 mg/ml, 0.05 to 2 mg/ml, 0.05 to 3 mg/ml, 0.05 to 4 mg/ml, 0.05 to 5 mg/ml, 0.05 to 7.5 mg/ml, 0.05 to 10 mg/ml, 0.075 to 1 mg/ml, 0.075 to 2 mg/ml, 0.075 to 3 mg/ml, 0.075 to 4 mg/ml, 0.075 to 5 mg/ml, 0.075 to 7.5 mg/ml, 0.075 to 10 mg/ml, 0.1 to 1 mg/ml, 0.1 to 2 mg/ml, 0.1 to 3 mg/ml, 0.1 to 4 mg/ml, 0.1 to 5 mg/ml, 0.1 to 7.5 mg/ml, 0.1 to 10 mg/ml, 0.25 to 1 mg/ml, 0.25 to 2 mg/ml, 0.25 to 3 mg/ml, 0.25 to 4 mg/ml, 0.25 to 5 mg/ml, 0.25 to 7.5 mg/ml, 0.25 to 10 mg/ml, 0.5 to 1 mg/ml, 0.5 to 2 mg/ml, 0.5 to 3 mg/ml, 0.5 to 4 mg/ml, 0.5 to 5 mg/ml, 0.5 to 7.5 mg/ml, 0.5 to 10 mg/ml, 0.75 to 1 mg/ml, 0.75 to 2 mg/ml, 0.75 to 3 mg/ml, 0.75 to 4 mg/ml, 0.75 to 5 mg/ml, 0.75 to 7.5 mg/m, 0.75 to 10 mg/ml, 1 to 2 mg/ml, 1 to 3 mg/ml, 1 to 4 mg/ml, 1 to 5 mg/ml, 1 to 7.5 mg/m, or 1 to 10 mg/ml. According to some embodiments, the concentration of the pyruvate is 0.01 mg/ml, 0.03 mg/ml, 0.05 mg/ml, 0.07 mg/ml, 0.09 mg/ml, 0.11 mg/ml, 0.13 mg/ml, 0.15 mg/ml, 0.17 mg/ml, 0.19 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, 2 mg/ml, 3 mg/ml, 4 mg/ml, 5 mg/ml, 6 mg/ml, 7 mg/ml, 8 mg/ml, 9 mg/ml or 10 mg/ml. According to preferred embodiments, the concentration of the pyruvate is 0.05 to 5 mg/ml.

Monothioglycerol (MTG)

According to some embodiments, the culture medium further comprises monothioglycerol (MTG).

According to the present disclosure, the concentration of MTG is not particularly limited as long as it can support the prolonged expansion of MSCs. According to some embodiments, the concentration of MTG is 1 to 200 μM, e.g., 1 to 5 μM, 1 to 10 μM, 1 to 15 μM, 1 to 20 μM, 1 to 25 μM, 1 to 30 μM, 1 to 35 μM, 1 to 40 μM, 1 to 45 μM, 1 to 50 μM, 1 to 60 μM, 1 to 70 μM, 1 to 80 μM, 1 to 90 μM, 1 to 100 μM, 1 to 150 μM, 1 to 200 μM, 2 to 5 μM, 2 to 10 μM, 2 to 15 μM, 2 to 20 μM, 2 to 25 μM, 2 to 30 μM, 2 to 35 μM, 2 to 40 μM, 2 to 45 μM, 2 to 50 μM, 2 to 60 μM, 2 to 70 μM, 2 to 80 μM, 2 to 90 μM, 2 to 100 μM, 2 to 150 μM, 2 to 200 μM, 3 to 5 μM, 3 to 10 μM, 3 to 15 μM, 3 to 20 μM, 3 to 25 μM, 3 to 30 μM, 3 to 35 μM, 3 to 40 μM, 3 to 45 μM, 3 to 50 μM, 3 to 60 μM, 3 to 70 μM, 3 to 80 μM, 3 to 90 μM, 3 to 100 μM, 3 to 150 μM, 3 to 200 μM, 4 to 5 μM, 4 to 10 μM, 4 to 15 μM, 4 to 20 μM, 4 to 25 μM, 4 to 30 μM, 4 to 35 μM, 4 to 40 μM, 4 to 45 μM, 4 to 50 μM, 4 to 60 μM, 4 to 70 μM, 4 to 80 μM, 4 to 90 μM, 4 to 100 μM, 4 to 150 μM, 4 to 200 μM, 5 to 10 μM, 5 to 15 μM, 5 to 20 μM, 5 to 25 μM, 5 to 30 μM, 5 to 35 μM, 5 to 40 μM, 5 to 45 μM, 5 to 50 μM, 5 to 60 μM, 5 to 70 μM, 5 to 80 μM, 5 to 90 μM, 5 to 100 μM, 5 to 150 μM, 5 to 200 μM, 10 to 15 μM, 10 to 20 μM, 10 to 25 μM, 10 to 30 μM, 10 to 35 μM, 10 to 40 μM, 10 to 45 μM, 10 to 50 μM, 10 to 60 μM, 10 to 70 μM, 10 to 80 μM, 10 to 90 μM, 10 to 100 μM, 10 to 150 μM or 10 to 200 μM. According to some embodiments, the concentration of MTG is 1 μM, 2 μM, 3 μM, 4 μM, 5 μM, 6 μM, 7 μM, 8 μM, 9 μM, 10 μM, 15 μM, 20 μM, 25 μM, 30 μM, 35 μM, 40 μM, 45 μM, 50 μM, 60 μM, 70 μM, 80 μM, 90 μM, 100 μM, 110 μM, 120 μM, 130 μM, 140 μM, 150 μM or 200 μM. According to preferred embodiments, the concentration of the MTG is 10 to 150 μM.

Nicotinamide (NAM)-Based Compound

According to some embodiments, the culture medium further comprises a nicotinamide-based compound.

As used herein, "nicotinamide-based compound" refers to nicotinamide, analogs thereof, metabolites of nicotinamide or nicotinamide analogs, such as, for example, NAD, NADH and NADPH, salts thereof, or mixtures thereof.

According to embodiments of the present disclosure, the nicotinamide-based compound may be selected from the group consisting of nicotinamide, a nicotinamide analog, a nicotinamide metabolite, a nicotinamide analog metabolite, and derivatives thereof.

Nicotinamide is the amide form of niacin, both of which belong to the vitamin B3 family. They are the precursors of nicotinamide adenine dinucleotide (NAD), which acts as a coenzyme in multiple cellular processes, including energy metabolism and DNA repair. Nicotinamide can be converted into nicotinamide mononucleotide (NMN) by nicotinamide phosphoribosyltransferase (NAMPT), which is then turned into NAD$^+$ by nicotinamide mononucleotide adenylyltransferase (NMNAT).

As used herein, "nicotinamide analog" refers to any molecule that is known to act similarly to nicotinamide. Examples of nicotinamide analogs include, without limitation, nicotinethioamides (the thiol analog of nicotinamide), and nicotinic acid. Examples of nicotinamide derivatives include, but are not limited to, substituted nicotinamide-based compound and nicotinethioamides, and N-substituted nicotinamide-based compound and nicotinethioamides.

Examples of the salts of nicotinamide, analogs thereof, metabolites thereof and derivatives thereof include, without limitation, nicotinamide hydrochloride, nicotinamide hydrobromide, and these salts of substituted nicotinamide.

According to preferred embodiments, the nicotinamide-based compound is nicotinamide.

According to the present disclosure, the concentration of the nicotinamide-based compound is not particularly limited as long as it can support the prolonged expansion of MSCs. According to some embodiments, the concentration of the nicotinamide-based compound is in the range of 0.1 to 30 mM, e.g., 0.1 to 5 mM, 0.1 to 10 mM, 0.1 to 15 mM, 0.1 to 20 mM, 0.1 to 25 mM, 0.1 to 30 mM, 0.3 to 5 mM, 0.3 to 10 mM, 0.3 to 15 mM, 0.3 to 20 mM, 0.3 to 25 mM, 0.3 to 30 mM, 0.5 to 5 mM, 0.5 to 10 mM, 0.5 to 15 mM, 0.5 to 20 mM, 0.5 to 25 mM, 0.5 to 30 mM, 0.75 to 5 mM, 0.75 to 10 mM, 0.75 to 15 mM, 0.75 to 20 mM, 0.75 to 25 mM, 0.75 to 30 mM, 1 to 5 mM, 1 to 10 mM, 1 to 15 mM, 1 to 20 mM, 1 to 25 mM, 1 to 30 mM, 2 to 5 mM, 2 to 10 mM, 2 to 15 mM, 2 to 20 mM, 2 to 25 mM, 2 to 30 mM, 3 to 5 mM, 3 to 10 mM, 3 to 15 mM, 3 to 20 mM, 3 to 25 mM, 3 to 30 mM, 4 to 5 mM, 4 to 10 mM, 4 to 15 mM, 4 to 20 mM, 4 to 25 mM, 4 to 30 mM, 5 to 10 mM, 5 to 15 mM, 5 to 20 mM, 5 to 25 mM, or 5 to 30 mM. According to some embodiments, the concentration of the nicotinamide-based compound is 0.1 mM, 0.2 mM, 0.3 mM, 0.4 mM, 0.5 mM, 0.6 mM, 0.7 mM, 0.8 mM, 0.9 mM, 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, or 30 mM. According to preferred embodiments, the concentration of the nicotinamide-based compound is 0.5 to 20 µM.

In certain embodiments, the culture medium comprises 5 to 30 µM of the ethanolamine-based compound, 1 to 20 µM of the putrescine-based compound, 0.1% to 10% by volume of HPLT, 1 to 150 µg/ml of transferrin, 1 to 10 µg/ml of the insulin-based compound, 1 to 150 µg/ml of the antioxidant, and 0.5% to 5% by volume of the glutamine or its derivative in the basal medium.

In certain embodiments, the culture medium comprises 5 to 30 µM of ethanolamine, 1 to 20 µM of putrescine dihydrochloride, 0.1% to 10% by volume of HPLT, 1 to 150 µg/ml of transferrin, 1 to 10 µg/ml of insulin, 1 to 150 µg/ml of ascorbate, and 0.5% to 5% by volume of glutamine in the basal medium.

In certain embodiments, the culture medium comprises 5 to 30 µM of ethanolamine, 1 to 20 µM of putrescine dihydrochloride, 0.1% to 10% by volume of HPLT, 1 to 150 µg/ml of transferrin, 1 to 10 µg/ml of insulin, 1 to 150 µg/ml of ascorbate, 0.5% to 5% by volume of glutamine, 1 to 15 ng/ml of FGF2, 0.5 to 5 µM of hydrocortisone, 1 to 10 µM of lipoic acid, 1 to 30 µM of FeSO$_4$, and 0.1 to 10 µM of Fe(NO$_3$)$_3$ in the basal medium.

In certain embodiments, the culture medium comprises 5 to 30 µM of ethanolamine, 1 to 20 µM of putrescine dihydrochloride, 0.1% to 10% by volume of HPLT, 1 to 150 µg/ml of transferrin, 1 to 10 µg/ml of insulin, 1 to 150 µg/ml of ascorbate, 0.5% to 5% by volume of glutamine, 1 to 15 ng/ml of FGF2, 0.5 to 5 µM of hydrocortisone, 5 to 20 ng/ml of Na$_2$SeO$_3$, 0.05 to 5 mg/ml of sodium pyruvate, 1 to 10 mg/ml of HSA, 10 to 150 µM of MTG, 0.5 to 20 mM of nicotinamide (NAM), and 10 to 100 µg/ml of heparin sodium in the basal medium.

In certain embodiments, the culture medium provides the expansion fold of about 13 to about 15 folds for MSCs at a high seeding density (e.g., 5×10$^4$ cells/well). In certain embodiments, the culture medium provides the expansion fold of about 15 to about 30 folds for MSCs at a high seeding density (e.g., 5×10$^4$ cells/well). In contrast, the control medium provides the expansion fold of about 8 to about 10 folds for MSCs at the same high seeding density (e.g., 5×10$^4$ cells/well).

In certain embodiments, the culture medium provides the expansion fold of about 650 to about 1×10$^3$ folds for MSCs at a low seeding density (e.g., 1×10$^3$ cells/well). In certain embodiments, the culture medium provides the expansion fold of about 1×10$^3$ to about 4.5×10$^3$ folds for MSCs at a low seeding density (e.g., 1×10$^3$ cells/well). In contrast, the control medium provides the expansion fold of about 500 to about 600 folds for MSCs at the same low seeding density (e.g., 1×10$^3$ cells/well).

In certain embodiments, the culture medium stably supports the prolonged expansion of MSCs with a flat PDT curve of from about 20 to about 24 hours. In contrast, the control medium provides a steep PDT curve of from about 25 to about 57 hours for MSCs during the prolonged expansion.

2. Kit

According to one aspect of the present invention, there is provided a kit comprising the above culture medium as disclosed herein. The culture medium can be packaged into suitable packaging material such as container. The kit can optionally include a specification of the culture medium or components in the culture medium or instructions for use of the culture medium or the components therein.

The container of the kit may generally include vial, flask, bottle or any other container, into which a component may be suitably placed. Where there is more than one component in the kit, the kit may also contain a second, third or other additional container into which the additional components may be separately placed. However, various combinations of components may be comprised in a container.

In certain embodiments, the culture medium is packaged into a container. In certain embodiments, the components of the culture medium are separately packaged into different containers.

The components of the kit may be provided in one or more liquid solutions. However, the component(s) of the kit may be also provided as dried powder(s). When the component(s) are provided as dried powder(s), the powder(s) can be reconstituted by the addition of a suitable solvent.

3. Expansion Method

According to one aspect of the present disclosure, there is provided a method for expanding mesenchymal stem cells (MSCs), the method comprising contacting the MSCs with the culture medium as disclosed herein.

In certain embodiments, the method further comprises seeding the MSCs at a density of about 500 cells/well to about 1×10⁵ cells/well. In certain embodiments, the method further comprises seeding the MSCs at a high density of about 5×10⁴ cells/well to about 1×10⁵ cells/well. In certain embodiments, the method further comprises seeding the MSCs at a low density of about 500 cells/well to about 1×10³ cells/well.

In certain embodiments, the method further comprises replacing the expansion medium with the same medium every several days during the expansion. In certain embodiments, the method further comprises replacing the expansion medium with the same medium every three days during the expansion.

In certain embodiments, the MSCs are continuously expanded for multiple passages. In certain embodiments, the MSCs are continuously expanded for at least 2 passages. In certain embodiments, the MSCs are continuously expanded for at least 3 passages. In certain embodiments, the MSCs are continuously expanded for at least 4 passages. In certain embodiments, the MSCs are continuously expanded for at least 5 passages. In certain embodiments, the MSCs are continuously expanded for at least 6 passages. In certain embodiments, the MSCs are continuously expanded for at least 7 passages. In certain embodiments, the MSCs are continuously expanded for at least 8 passages. In certain embodiments, the MSCs are continuously expanded for at least 9 passages.

According to the present disclosure, the MSCs produced by the method as disclosed herein are substantially homogeneous cell populations even if the MSCs are continuously expanded for multiple passages such as at least 4, 7 or 9 passages. To be specific, the MSCs produced by the method as disclosed herein can maintain the MSC characteristics such as morphology, phenotype, differentiation potential and immunomodulatory effect even if the MSCs are continuously expanded for multiple passages.

4. Cell Populations

According to one aspect of the present disclosure, there is provided a substantially homogeneous population of MSCs produced by the method of the present disclosure.

According to some embodiments, the substantially homogeneous population of MSCs is a cell population of at least passage 2 (P2), at least 4 passage (P4), at least 7 passage (P7), or at least passage 9 (P9). According to some embodiments, the substantially homogeneous population of MSCs is a cell population of passage 2, passage 3, passage 4, passage 5, passage 6, passage 7, passage 8 or passage 9.

According to certain embodiments, the population of MSCs of the present disclosure can be cryopreserved or stored for further expansion and/or differentiation.

According to the present disclosure, the substantially homogeneous population of MSCs has a higher percentage of CD90⁺ cells during the prolonged expansion. In certain embodiments, the substantially homogeneous population of MSCs comprises at least 90% of CD90⁺ cells. In certain embodiments, the substantially homogeneous population of MSCs comprises at least 95% of CD90⁺ cells. In certain embodiments, the substantially homogeneous population of MSCs comprises at least 99% of CD90⁺ cells. In certain embodiments, the substantially homogeneous population of MSCs comprises 90%, 91%, 92%, 93%, 94%, 95%, 96%, 97%, 98%, or 99% of CD90⁺ cells.

EXAMPLES

The following examples demonstrate some embodiments of the present invention. However, it is to be understood that these examples are for illustration only and do not purport to be wholly definitive as to conditions and scope of this invention.

Furthermore, the following examples were carried out using standard techniques, which are well known and routine to those of skill in the art, except where otherwise described in detail. As noted above, the following examples are presented for illustrative purpose, and should not be construed in any way limiting the scope of this invention.

Materials

All reagents and apparatuses utilized throughout the Examples of the present disclosure are commercially available. Certain reagents used in the Examples are listed below.

TABLE 1

| Reagents | Company |
| --- | --- |
| IMDM | Sigma |
| IMDM basal (+NaHCO₃) | Sigma |
| DMEM/F12 | Gibco |
| Ham's F12 | Sigma |
| Ultroser G (Serum Replacement (SR)) | Pall |
| Glutamax | Thermo |
| Insulin | BIOING BIOLOGICALS |
| Transferrin | Sigma |
| Mg Ascorbate | Sigma |
| Ethanolamine | Sigma |
| Putrescine 2HCl | Sigma |
| NaHCO₃ | Sigma |
| HEPES | Sigma |
| HSA | Chengdu Rongsheng Pharmaceuticals Co., Ltd. |
| 2-Mercaptoethanol | Sigma |
| chemically defined lipids | Invitrogen |
| fibronectin | Sigma |
| pluronic F-68 | Gibco |
| hydrocortisone | Tocris |
| progesterone | Sigma |
| Heparin sodium | Thermo fisher |
| serotonin | Sigma |
| EGF | Peprotech |
| FGF2 | Nuwacell Co., Ltd. |
| PDGF-BB | Peprotech |
| IGF-1 | Peprotech |
| IL-3 | Peprotech |
| GM-SCF | Peprotech |
| TGFβ1 | Peprotech |
| Monothioglycerol (MTG) | Sigma |
| Trace element A (1000x) | Mediatech |
| Trace element B (1000x) | Mediatech |
| lipoic acid | Sigma |
| FeSO₄ | Sigma |
| Fe(NO₃)₃ | Sigma |
| B27 | Thermo |
| N2 | Thermo |
| KOSR | Thermo |
| HPLT | Biological Industries |
| BIT9500 | SCT |
| Na₂SeO₃ | Sigma |
| Sodium pyruvate | Sigma |
| nicotinamide | Sigma |

Examples 1-4

The present examples were carried out in order to demonstrate that HPLT was crucial for supporting the prolonged expansion of iMSCs.

Example 1

Cryopreserved iMSCs (RC01005, Nuwacell Co., Ltd.) were seeded in 6-well plates at 1000 cells/well in M1 medium to thaw the cells. The above medium was replaced 24 h later with 2 ml/well of the following medium: M1, SFM-M, PPRF, or MEM-FBS. M1 medium contained IMDM (+NaHCO₃)/F12 (50%/50%), 2% by volume of Ultroser G (a Serum Replacement (SR)), 1% by volume of Glutamax, 1-150 μg/ml (e.g., 120 μg/ml) of transferrin, 5 μg/ml of insulin, 1-150 μg/ml (e.g., 110 μg/ml) of Mg Ascorbate, 20 μM of Ethanolamine, and 10 μM of Putrescine 2HCl. SFM-M contained IMDM/F12 (50%/50%), 1% by volume of Glutamax, 5 μg/ml of insulin, 5 μg/ml of transferrin, 50 μg/ml of Mg Ascorbate, 4 mg/ml of HSA, 50 nM of 2-Mercaptoethanol, 0.10% of chemically defined lipids, 1 μg/ml of fibronectin, 100 μg/ml of pluronic F-68, 50 ng/ml of hydrocortisone, 15 ng/ml of progesterone, 10 IU/ml of heparin sodium, 2 μg/ml of serotonin, 10 ng/ml of EGF, 10 ng/ml of FGF2, 10 ng/ml of PDGF-BB, 10 ng/ml of IGF-1, 1 ng/ml of IL-3, and 1 ng/ml of GM-SCF. PPRF medium contained F12, 2% by volume of Glutamax, 25 μg/ml of insulin, 25 μg/ml of transferrin, 50 μg/ml of Mg Ascorbate, 55.9 μM of Putrescine 2HCl, 20.5 mM of NaHCO₃, 4.9 mM of HEPES, 4 mg/ml of HSA, 0.10% of chemically defined lipids, 36 ng/ml of hydrocortisone, 5.66 ng/ml of progesterone, 2 ng/ml of FGF2, and 1 ng/ml of TGFβ1. MEM-FBS medium contained 90% (v/v) αMEM and 10% (v/v) FBS. During subsequent cell culture, the medium was changed with the same medium every three days. On day 10 of culture, the cells were observed and photographed using a phase contrast microscope. The cell morphologies of iMSCs cultured in the above different culture media were shown in FIG. 1.

As shown in FIG. 1, the cells cultured in M1 and MEM-FBS expanded well, but the cells cultured in the other media (SFM-M and PPRF) could not expand. Although it had been proven by the present inventors in the above example that M1 and MEM-FBS media were able to support iMSC expansion, the Ultroser G contained in M1 as the main component contained animal-derived components and the FBS contained in the MEM-FBS medium was also an animal-derived serum, which was not a good choice for clinical applications. So developing a serum-free and xeno-free medium for MSC (e.g., iMSC) expansion would be of great clinical significance.

Example 2

Cryopreserved iMSCs (RC01005, Nuwacell Co., Ltd.) were seeded in 6-well plates at 50000 cells/well in M1 medium to thaw the cells. The medium was replaced 24 h later with 2 ml/well of the following medium: M1 or M2. M1 medium had the composition as described in the Example 1 and was used as a control. As compared with M1 medium, M2 medium had the same composition except for substituting HPLT for Ultroser G. M2 medium contained indicated concentration (1%, 2%, 3%, 4% or 5% by volume) of HPLT. On day 4 of culture, the cells were digested by solase (RP01021, Nuwacell Co., Ltd.) for 3 min and collected, and then centrifugated, and with the supernatant removed, resuspended in corresponding medium, and the number of iMSC cells was counted by cell viability analyzer (Vi-CELLTMXR, BECKMAN COULTER). Before the digestion, the cells were observed and photographed using a phase contrast microscope. The cell morphology of iMSCs was shown in FIG. 2A and the cell number of iMSCs was shown in FIG. 2B.

Figure 2A:
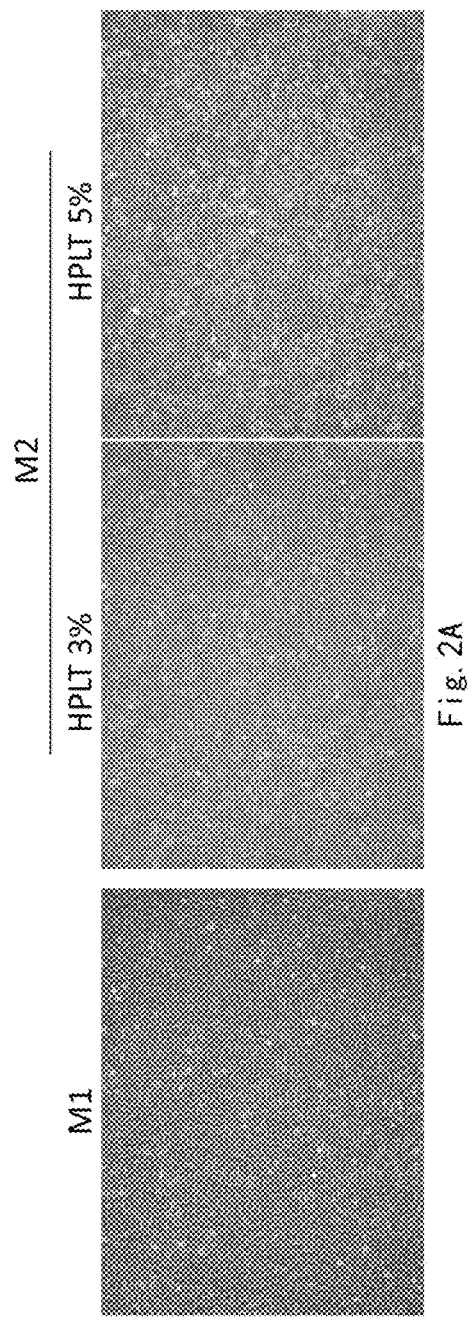
Figure 2B:
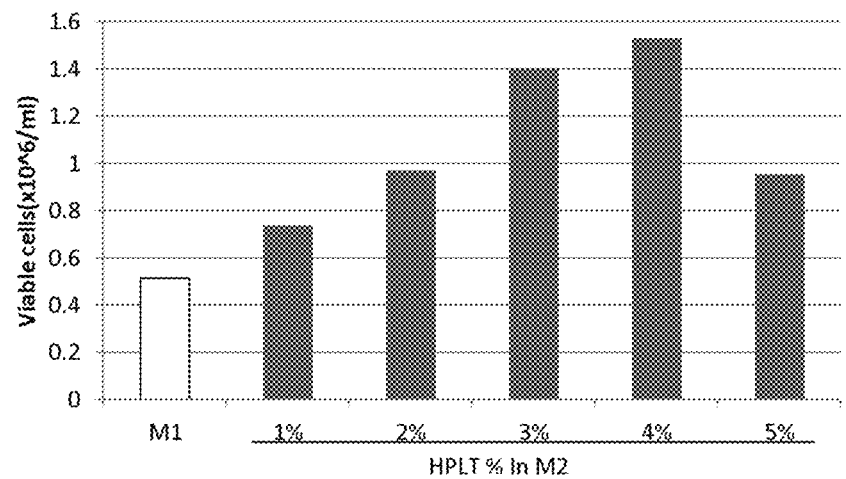

As shown in FIG. 2A, the iMSC cells cultured in M2 with HPLT were found to expand well and could retain their original morphological characteristics (Like spindle shaped fibroblasts) similar to those cultured in M1 medium. As shown in FIG. 2B, the cell number of the iMSC cells cultured in M2 with HPLT was significantly higher than that of the iMSC cells cultured in M1 with Ultroser G (the former was about 1.5 to about 3 times the latter), which showed that the replacement of Ultroser G with HPLT could not only avoid the use of the animal-derived components, but also greatly improved the expansion efficiency of the iMSC cells. In addition, FIG. 2B showed that different concentrations of HPLT could affect the expansion efficiency of the iMSCs at a certain degree.

Example 3

Figure 3A:
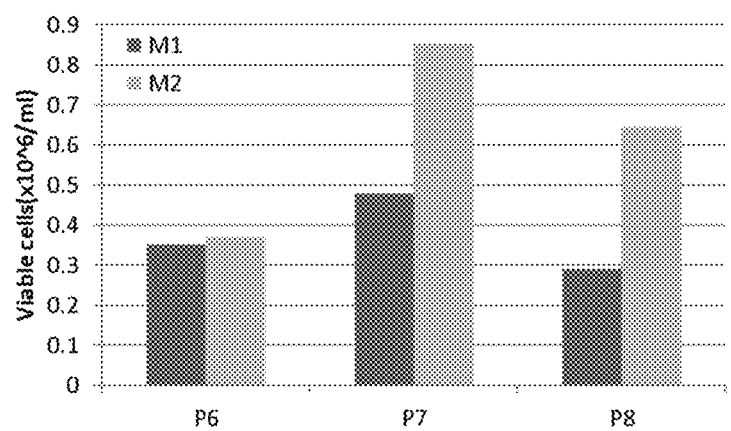
Figure 3B:
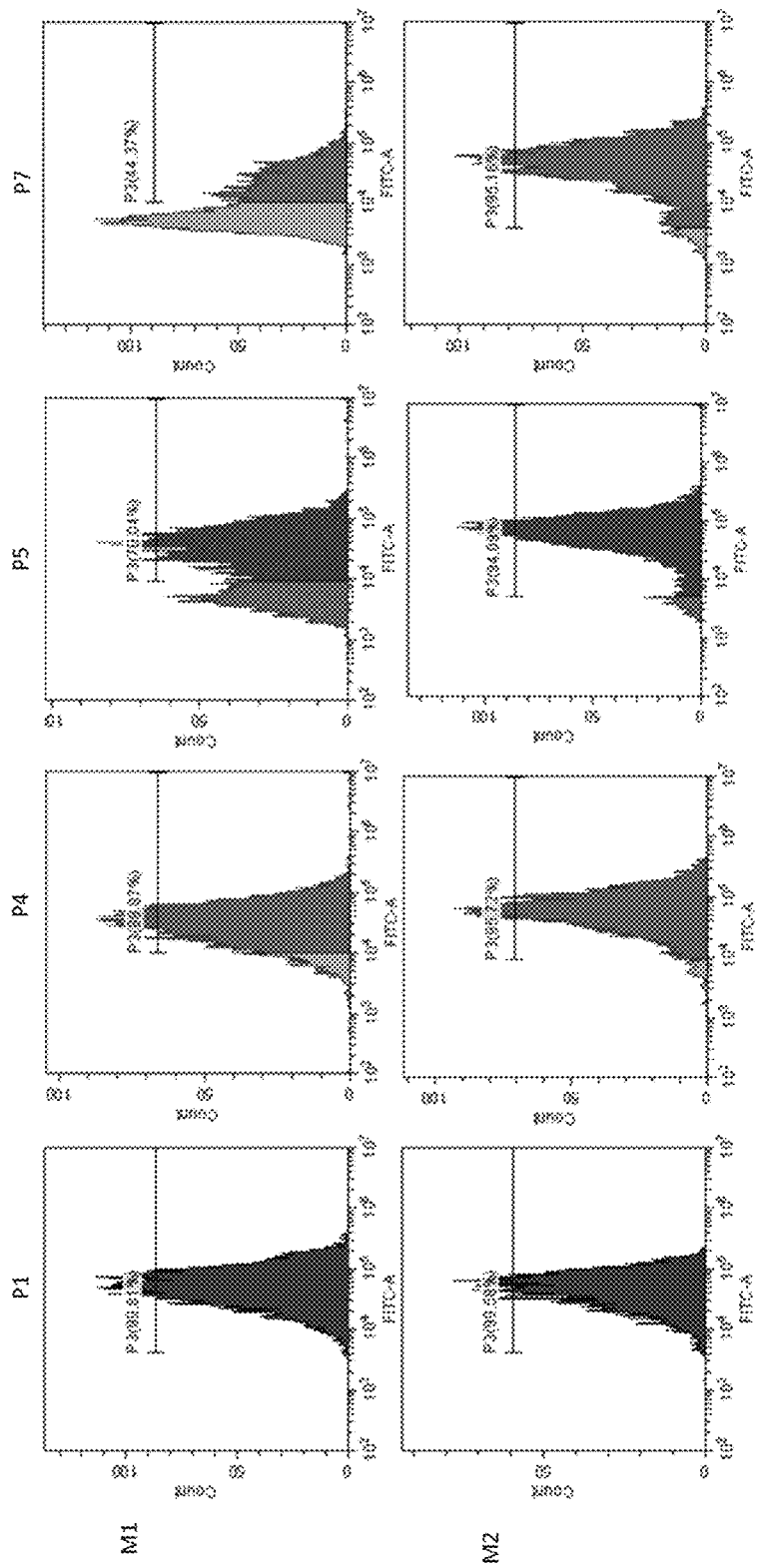

Cryopreserved iMSCs (RC01005, Nuwacell Co., Ltd.) were seeded in 6-well plates at 50000 cells/well in M1 medium to thaw the cells. The medium was replaced 24 h later with 2 ml/well of M1 or M2 (3% HPLT). M1 medium had the composition as described in the Example 1 and was used as a control. M2 (3% HPLT) had the same composition as that described in the Example 2. The iMSCs were continuously cultured and passaged. The cell number of each passage from passage 6 to passage 8 was counted by cell viability analyzer (Vi-CELLTMXR, BECKMAN COULTER) according to the protocol as described in Example 2 (FIG. 3A).

iMSCs of passage 1, 4, 5 and 7 were stained with CD90-FITC antibody (BD Pharminge, 555595), and the percentage of CD90⁺ cells was detected by flow cytometry analysis (FIG. 3B). In brief, cells were digested by solase (RP01021, Nuwacell Co., Ltd.) for 3 min, resuspended in an assay buffer (0.5% BSA and 0.5 mM EDTA in DPBS), and adjusted to a density of $5\times10^5$-$1\times10^6$ cells/tube. After incubation with the CD90-FITC antibody at 4° C. for 30 min, the samples were washed with the assay buffer, and with the assay buffer removed, resuspended in 100 μl of the assay buffer, and the percentage of CD90⁺ cells was analyzed using a flow cytometer (CytoFLEX, BECKMAN COULTER).

As shown in FIG. 3A, the iMSCs cultured in M2 had higher cell number than the iMSCs cultured in M1 for all of P6, P7 and P8 cells, which showed that the replacement of the Ultroser G with HPLT could improve the expansion efficiency for each passage of iMSC cells and in particular high passage of iMSC cells. As shown in FIG. 3B, in case where iMSCs were cultured using M1, CD90-expressing cells were quickly reduced from 99.81% of P1 to 88.87% of P4, 70.04% of P5 and 44.37% of P7, which showed that M1 couldn't stably maintain the stem cell phenotype of iMSCs during the prolonged expansion of the iMSCs. In particular, CD90-expressing cells were more quickly reduced with the prolonged expansion of iMSCs. In contrast, in case where iMSCs were cultured using M2, the proportion of CD90-expressing cells was more stably maintained from P1 to P7. Accordingly, the data in FIGS. 3A and 3B showed that the replacement of the Ultroser G with HPLT could improve the expansion efficiency for the cells of each passage and more stably maintain the stem cell phenotype of iMSCs during the prolonged expansion. In addition, in case where iMSCs were cultured using M2, some small peaks arised on the left side with the prolonged expansion of the iMSCs (FIG. 3B).

Example 4

CFSE-based T cell proliferation assay was used to evaluate the immunosuppressive effect of iMSCs. To expand T cells, PBMCs were activated by immobilized CD3 antibody (biogerm, 05121-25-100) and CD28 antibody (biogerm, 10311-25-100) in TPA medium (T cell proliferation assay medium, RPMI 1640+10% (v/v) FBS+1% (v/v) Glutamax) supplemented with 100 IU/ml IL-2 (Jiangsu Jinsili Pharmaceutical Co., Ltd, china) for 4 days. Activated T cells were collected, then stained with CFSE (Ab145291, Abcam), and co-cultured with or without the two types of iMSCs cultured according to Example 3 for 5 days. Specifically, the iMSCs of passage 3 were treated with Mitomycin C to block cell proliferation before co-culture with T cells. T cells were then added to the treated iMSCs at a ratio of 1:1. The cell morphology on day 5 of the co-culture was shown in the FIG. 4A. The percentage of divided T cell population (dark gray, CFSE-low population) was detected by flow cytometry according to the protocol as described in Example 3 (FIG. 4B).

Figure 4A:
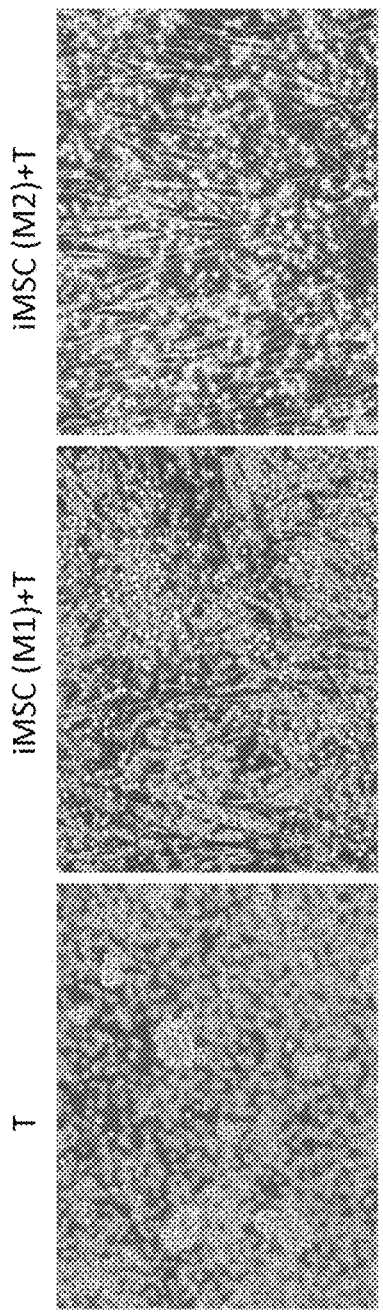
Figure 4B:
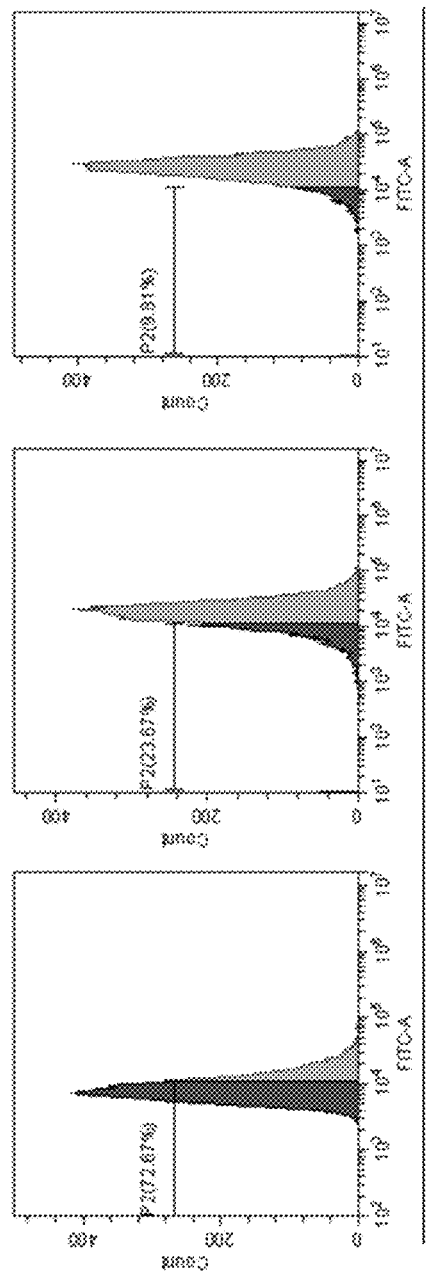

As shown in FIG. 4A, the cell division of T cell cultured without any iMSCs was highly activated, so the fluorescence intensity of CFSE was significantly reduced (the peak moved to the left side), but the expansion of T cells cultured with the iMSCs was significantly inhibited (the peak hardly moved) (FIG. 4B). In addition, the iMSCs cultured in M2 had the comparable immunosuppressive effect to those cultured in M1, as shown by the percentage of divided T cell population. Accordingly, the data in FIG. 4 showed that the iMSCs of P3 cultured in M2 retained the immunosuppressive effect for T cells.

The above examples 1-4 demonstrated that, although M1 medium containing ethanolamine and putrescine 2HCl could support the expansion of iMSCs, it couldn't stably maintain the stem cell phenotype (CD90 expression) of iMSCs during the prolonged expansion due to lack of HPLT, while M2 medium with all of ethanolamine, putrescine 2HCl, and HPLT could stably maintain the stem cell phenotype (CD90 expression) of iMSCs during the prolonged expansion. This demonstrated that HPLT was crucial for stably maintaining the stem cell phenotype of iMSCs during the prolonged expansion.

In addition, as compared with M1 medium, M2 medium avoided the use of the animal-derived components, and could promote robust iMSC proliferation and provide iMSCs with the comparable immunosuppressive effect.

In summary, by combining the results of Examples 1-4, M2 was found to support the prolonged expansion of iMSCs without losing MSC characteristics (including morphology, phenotype, differentiation potential and immunomodulatory effect), indicating the high potential of M2 in clinical applications.

Example 5

The present example was carried out in order to demonstrate that FGF2 and/or hydrocortisone could further promote the iMSC expansion.

Cryopreserved iMSCs (RC01005, Nuwacell Co., Ltd.) were seeded in 6-well plates at 1000 cells/well in M1 medium to thaw the cells. The medium was replaced 24 h later with 2 ml/well of the following medium: M1; or M2 (5% HPLT) further supplemented with or without one or more growth factors (F: FGF2 (10 ng/ml, Nuwacell Co., Ltd.); P: PDFG-BB (10 ng/ml, Cat. No.: 100-14B-100, Peprotech); T: TGFβ1 (1 ng/ml, Cat. No.: 100-21, Peprotech)) in the absence or presence of hydrocortisone (1 µM, Cat. No.: 4098, Tocris). M1 medium had the composition as described in the Example 1 and was used as a control. M2 (5% HPLT) had the same composition as that described in the Example 2. The medium was changed with the same medium every three days. On day 10 of culture, the cells were digested by solase (RP01021, Nuwacell Co., Ltd.) for 3 min and collected, and then centrifugated, and with the supernatant removed, resuspended in the corresponding medium, and the number of iMSC cells was counted by cell viability analyzer (Vi-CELLTMXR, BECKMAN COULTER) (FIG. 5).

Figure 5:
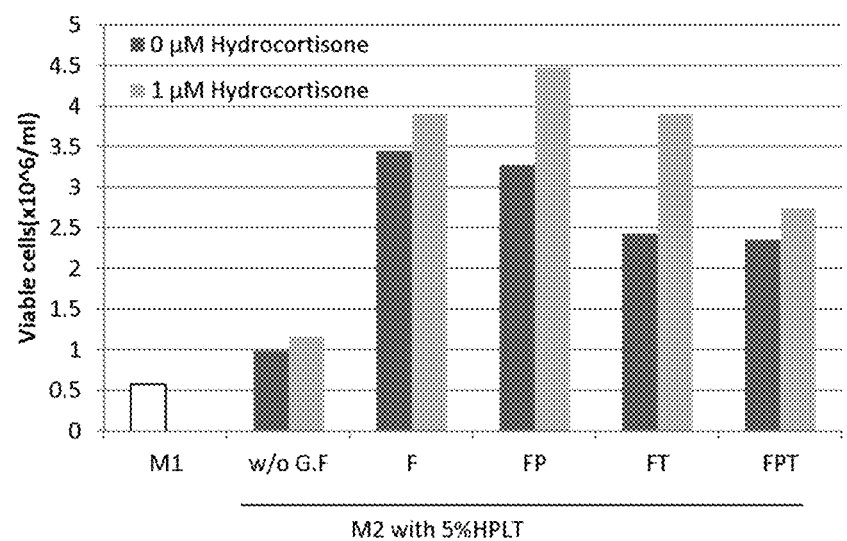
FIG. 5 shows the effects of different types of growth factors and different concentrations of hydrocortisone in the expansion medium on the proliferation of iMSCs according to Example 5, wherein F represents FGF2, FP represents the combination of FGF2 (F) and PDFG-BB (P), FPT represents the combination of FGF2 (F), PDFG-BB (P) and TGFβ1 (T), and w/o G.F represents the case without any growth factors.

As shown in FIG. 5, regardless of the presence or absence of hydrocortisone, the cell number of the iMSCs cultured in M2 (5% HPLT) further supplemented with only FGF2, the combination of FGF2 with PDFG-BB or TGFβ1, or the combination of FGF2, PDFG-BB and TGFβ1 was not only significantly higher than that of the iMSCs cultured in M1 (the former was about 4.5 to about 9 times the latter), but also greatly outperformed the iMSCs cultured in M2 (5% HPLT) without any growth factor (the former was about 2.3 to about 3.75 times the latter), which showed that the addition of one or more growth factors could obviously promote the iMSC expansion. Furthermore, the addition of hydrocortisone could promote the iMSC proliferation, and in particular, in the presence of the indicated growth factors, the addition of hydrocortisone obviously promoted the iMSC expansion.

Examples 6-10

The present examples were carried out in order to demonstrate that ethanolamine and putrescine 2HCl were crucial for supporting the prolonged expansion of iMSCs.

Example 6

Figure 6A:
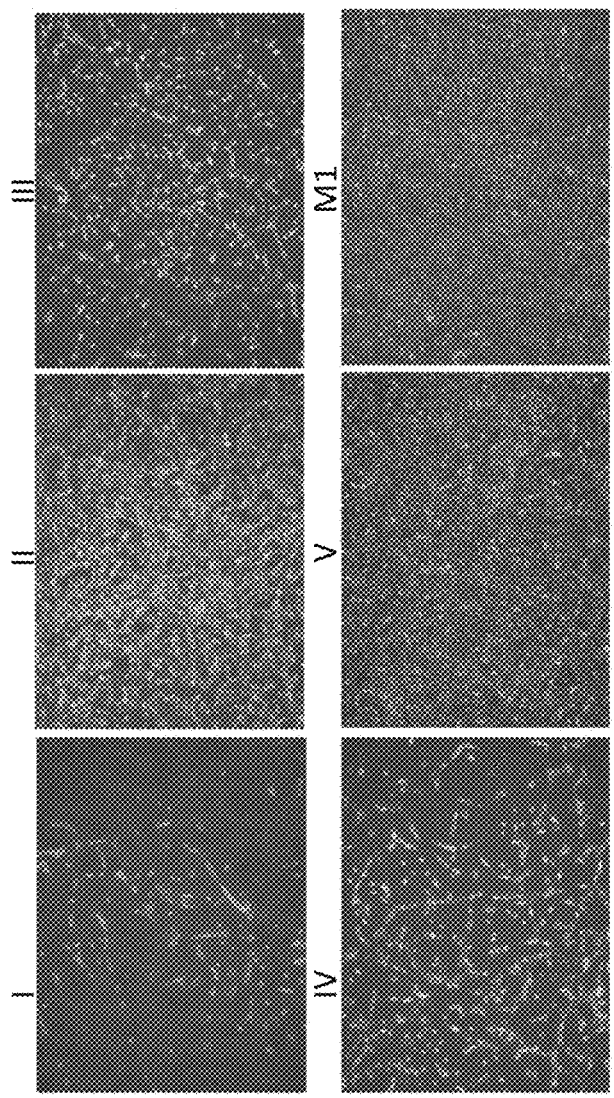
Figure 6B:
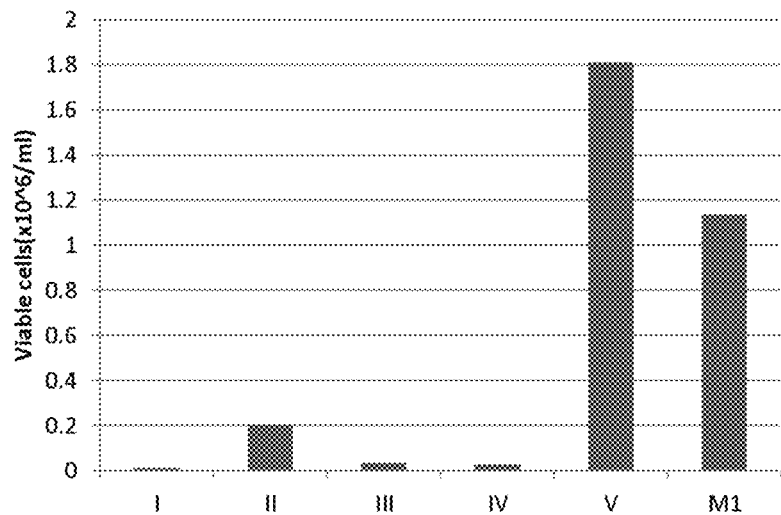

Cryopreserved iMSCs (RC01005, Nuwacell Co., Ltd.) were seeded in 6-well plates at 1000 cells/well in M1 medium to thaw the cells. The medium was replaced 24 h later with 2 ml/well of the following medium: I, II, III, IV, V or M1. M1 medium had the composition as described in the Example 1. Medium I contained IMDM basal (+NaHCO$_3$) (50%), Ham's F12 (50%), 1-150 µg/ml (e.g., 110 µg/ml) of Mg Ascorbate, 20 µM of Ethanolamine, 23.2 nM of Progesterone, 10 µM of Putrescine 2HCl, 5 µg/ml of Insulin, 1-150 µg/ml (e.g., 120 µg/ml) of transferrin, 100 µM of Monothioglycerol (MTG), 0.1% by volume of Chemically defined lipids, 0.1% by volume of Trace element A (1000×), 0.1% by volume of Trace element B (1000×), 1 µM of Hydrocortisone, 1% by volume of Glutamax, 10 ng/ml of FGF2, 10 ng/ml of PDGF-BB, and 4 mg/ml of HSA. Medium II had the same composition as medium I except for further adding 10% by volume of KOSR thereto. Medium III had the same composition as medium I except for further adding 2% by volume of B27 thereto. Medium IV had the same composition as medium I except for further adding 2% by volume of B27 and 1% by volume of N2 thereto. Medium V contained IMDM basal (+NaHCO$_3$) (100%), 1-150 µg/ml (e.g., 110 µg/ml) of Mg Ascorbate, 5 µg/ml of Insulin, 1-150 µg/ml (e.g., 120 µg/ml) of transferrin, 1 µM of Hydrocortisone, 4 ng/ml of FGF2, 1-10 µM (e.g., 10 µM) of lipoic acid, 1-30 µM (e.g., 30 µM) of FeSO$_4$, 0.1-10 µM (e.g., 10 µM) of Fe(NO$_3$)$_3$, and 20% by volume of BIT9500. The medium was changed with the same medium every three days. The cell morphology of day 10 culture was shown in FIG. 6A, and the cell number was counted by cell viability analyzer (Vi-CELLTMXR, BECKMAN COULTER) according to the protocol as described in Example 5 (FIG. 6B).

As shown in FIG. 6, among medium I, II, III, IV and V, only medium V (also called as EPM) was able to support iMSC expansion and significantly out-performed M1. Similar to M1, medium V also contained a serum replacement, BIT9500, which was not a good choice for clinical applications.

Example 7

Cryopreserved ucMSCs (RC02003, Nuwacell Co., Ltd.) and iMSCs (RC01005, Nuwacell Co., Ltd.) were seeded in 6-well plates at 50000 cells/well in M1 medium to thaw the cells. The medium was replaced 24 h later with 2 ml/well of the following medium: M1 or M3. M1 medium had the composition as described in the Example 6 and was used as a control. M3 had the same composition as EPM shown in the Example 6 except for substituting HPLT for BIT9500. M3 medium contained indicated concentration (1%, 2%, 3%, 4% or 5% by volume) of HPLT. On day 4 of culture, when cells got confluent, the cell number of iMSCs was counted by cell viability analyzer (Vi-CELLTMXR, BECKMAN COULTER) according to the protocol as described in Example 2.

Figure 7:
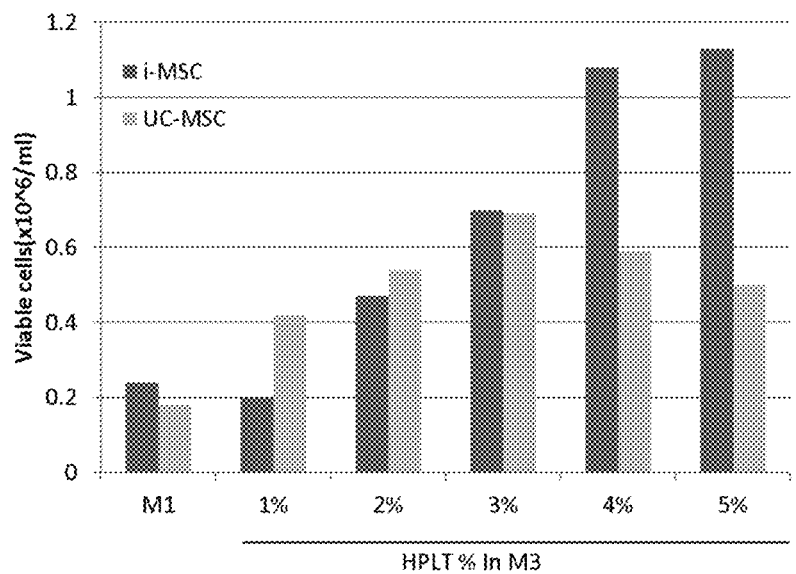
FIG. 7 shows the different effects of M1 and M3 media with different concentrations of HPLT on the proliferation of umbilical cord-derived mesenchymal stem cells (ucMSCs) and iMSCs according to Example 7.

As shown in FIG. 7, the cell number of the ucMSCs or iMSCs cultured in M3 with HPLT was substantially higher than those of the ucMSC or iMSCs cultured in M1 with the Ultroser G. Accordingly, HPLT was found to perfectly substitute BIT9500 in EPM, with a concentration-dependent effect in promoting both ucMSC and iMSC proliferation. This demonstrated that M3 media were able to support MSC (iMSC and ucMSC) expansion due to the presence of HPLT.

Example 8

Cryopreserved iMSCs (RC01005, Nuwacell Co., Ltd.) were seeded in 6-well plates at 50000 cells/well in M1 medium to thaw the cells. The medium was replaced 24 h later with 2 ml/well of the following medium: M1, M3 (3% HPLT), M4. M1 and M3 (3% HPLT) media had the same composition as those shown in the Example 7 and were used as controls. As compared with M3 (3% HPLT), M4 had the same composition except for further adding 10 µM of putrescine 2HCl and 20 µM of ethanolamine thereto. On day 4 of culture, when cells got confluent, the cell number of iMSCs was counted by cell viability analyzer (Vi-CELLTMXR, BECKMAN COULTER) according to the protocol as described in Example 2.

Figure 8:
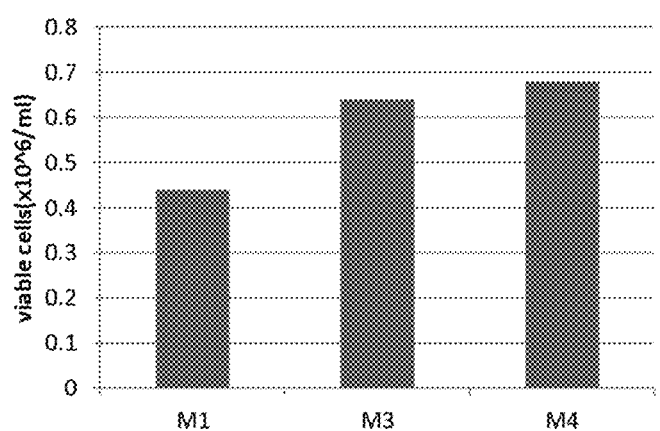
FIG. 8 shows the effect of different media, M1, M3 and M4, on the proliferation of iMSCs according to Example 8.

As shown in FIG. 8, the cell number of the iMSCs cultured in M4 not only significantly outperformed that of the iMSCs cultured in M1 (the former was about 1.5 times the latter), but also was slightly higher than that of the iMSCs cultured in M3. This demonstrated that M4 was able to support iMSC expansion.

Example 9

Cryopreserved iMSCs (RC01005, Nuwacell Co., Ltd.) were seeded in 6-well plates at 50000 cells/well in M1 medium to thaw the cells. The medium was replaced 24 h later with 2 ml/well of the following medium: M1, M3 (3% HPLT), or M4. iMSCs were cultured and passaged for 4 passages in the indicated medium. M1, M3 (3% HPLT), and M4 had the composition as those in the example 8. The cells of P1 or P4 were stained with CD90-FITC antibody (BD Pharmingen, 555595) and the percentage of CD90$^+$ cells were detected by flow cytometry according to the protocol as described in Example 3.

Figure 9:
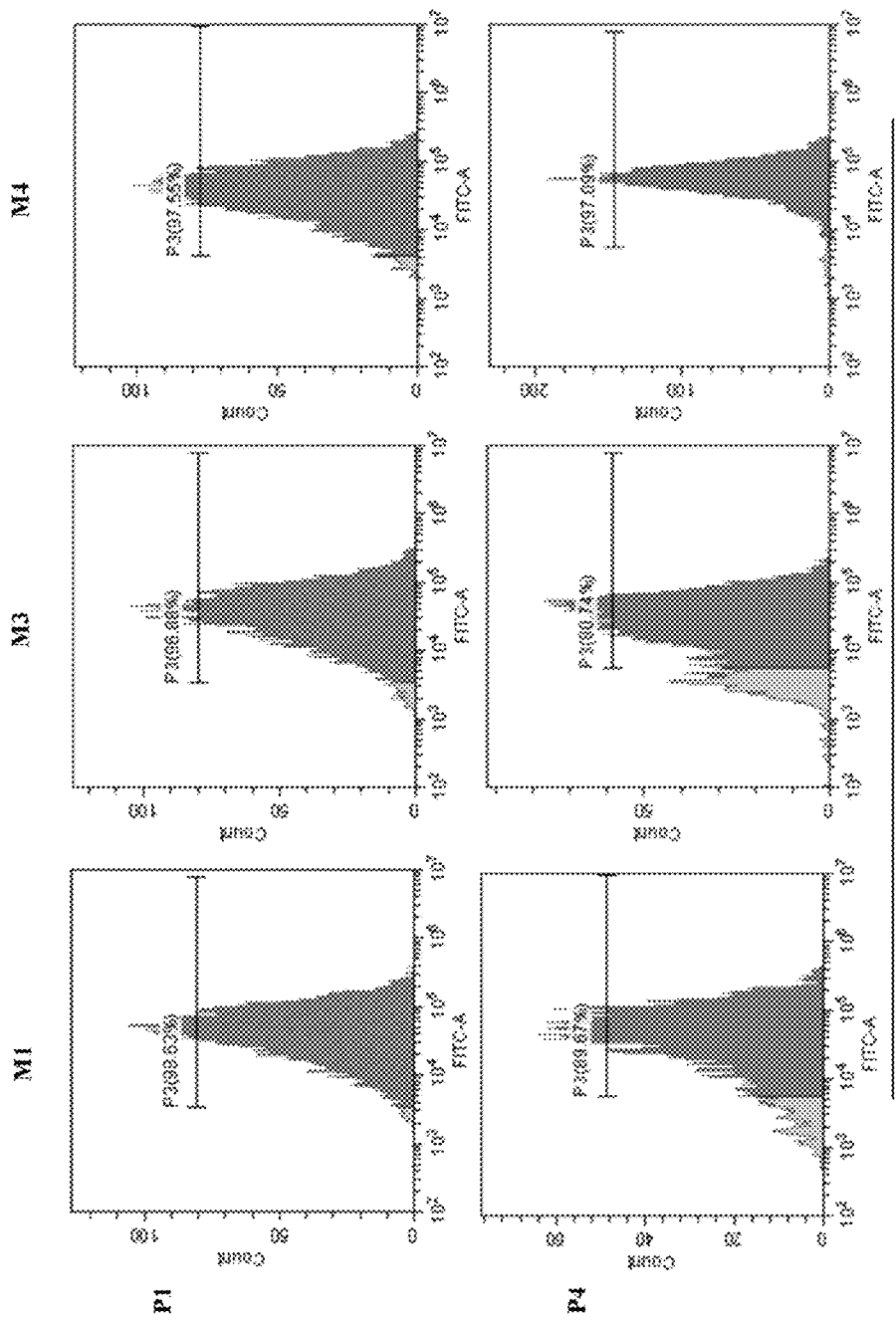
FIG. 9 shows the effect of different media, M1, M3 and M4, on the CD90 expression of expanded iMSCs according to Example 9.

Surprisingly, M4 maintained the stem cell phenotype of iMSCs better than both M1 and M3 as shown by the higher percentage of CD90$^+$ cells (FIG. 9). In detail, as shown in FIG. 9, CD90-expressing cells cultured using M1 were quickly reduced from 98.63% of P1 to 89.67% of P4, and CD90-expressing cells cultured using M3 were quickly reduced from 96.88% of P1 to 80.74% of P4, which showed that M1 and M3 could not stably maintain the stem cell phenotype of iMSCs during the prolonged expansion of iMSCs. In contrast, the proportion of CD90-expressing cells cultured using M4 was more stably maintained from P1 to P4. Accordingly, the data in FIG. 9 showed that inclusion of ethanolamine and putrescine 2HCl could stably maintain the stem cell phenotype of iMSCs during the prolonged expansion.

Example 10

Figure 10A:
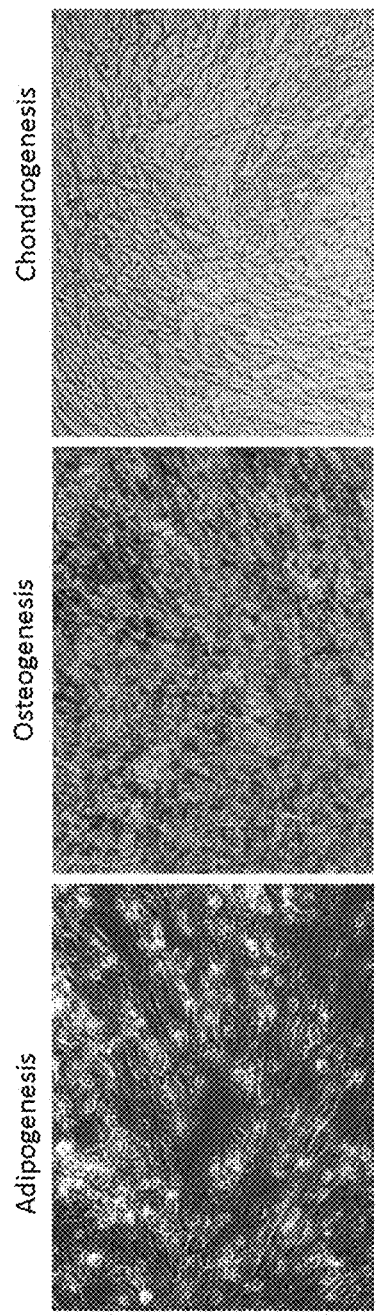

Cryopreserved iMSCs (RC01005, Nuwacell Co., Ltd.) were seeded in 6-well plates at 50000 cells/well in M1 medium to thaw the cells. The medium was replaced 24 h later with 2 ml/well of the following medium: M1, or M3 (3% HPLT). M1 and M3 (3% HPLT) had the composition as those in the example 9. iMSCs (RC01005, Nuwacell Co., Ltd.) were cultured in M3 (3% HPLT) and passaged for 4 passages and characterized as follows:

1. Osteogenic Differentiation iMSCs of P3 cultured in M3 (3% HPLT) were seeded in 6-well-plates. When the culture reached a confluence of 90%, the medium was replaced with an osteogenic differentiation medium (αMEM medium (Cat No.: 11900-024, thermo) supplemented with 20% by volume of FBS (Cat No.: SH30071.03, Hyclone), 1% Glutamax, 50 µg/ml ascorbic acid and 5 mM β-glycerophosphate (Cat No.: G9422, sigma)). The medium was changed with the same medium every three days until day 21. On day 21, the osteogenically differentiated cells were stained with Alizarin Red (Cat No.: 0223, ScienCell™) and the cell morphology was shown in FIG. 10A (middle panel).

2. Chondrogenic Differentiation

5×10$^5$/tube of iMSCs cultured in M3 (3% HPLT) were suspended in a chondrogenic differentiation medium (DMEM-HG medium (Cat. No.: 11960-069, Thermo) supplemented with 1 µM of ascorbic acid, 100 nM of dexamethasone (Cat. No.: D8893, Sigma), 1% of ITS+ premix tissue culture supplements (Cat. No.: 354352, Corning), 10 ng/ml of TGFβ1 (Cat. No.: 100-21-6, PeproTech) and 1% of sodium pyruvate (Cat. No.: 11360-070, Thermo)) in 15 mL centrifuge tube with the cap unscrewed. The medium was changed with the same medium every three days until day 28. On day 28, the cell spheres were stained with alcian blue (Cat. No.: A105505, aladdin) and the cell morphology was shown in FIG. 10A (right panel).

3. Adipogenic Differentiation iMSCs cultured in M3 (3% HPLT) were seeded in 6-well-plates. When the culture reached a confluence of 90%, the medium was replaced with an adipogenic differentiation medium (DMEM-HG medium supplemented with 45 µM of IBMX (Cat. No.: 15879, Sigma), 0.5 µM of dexamethasone (Cat. No.: D8893, Sigma), 50 µM of indomethacin (Cat. No.: I7378, Sigma) and 10% of FBS. The medium was changed with the same medium every three days until day 21. On day 21, the adipogenically differentiated cells were stained with Oil red O (Cat. No.: O0625, Sigma Aldrich) and the cell morphology was shown in FIG. 10A (left panel).

Figure 10B:
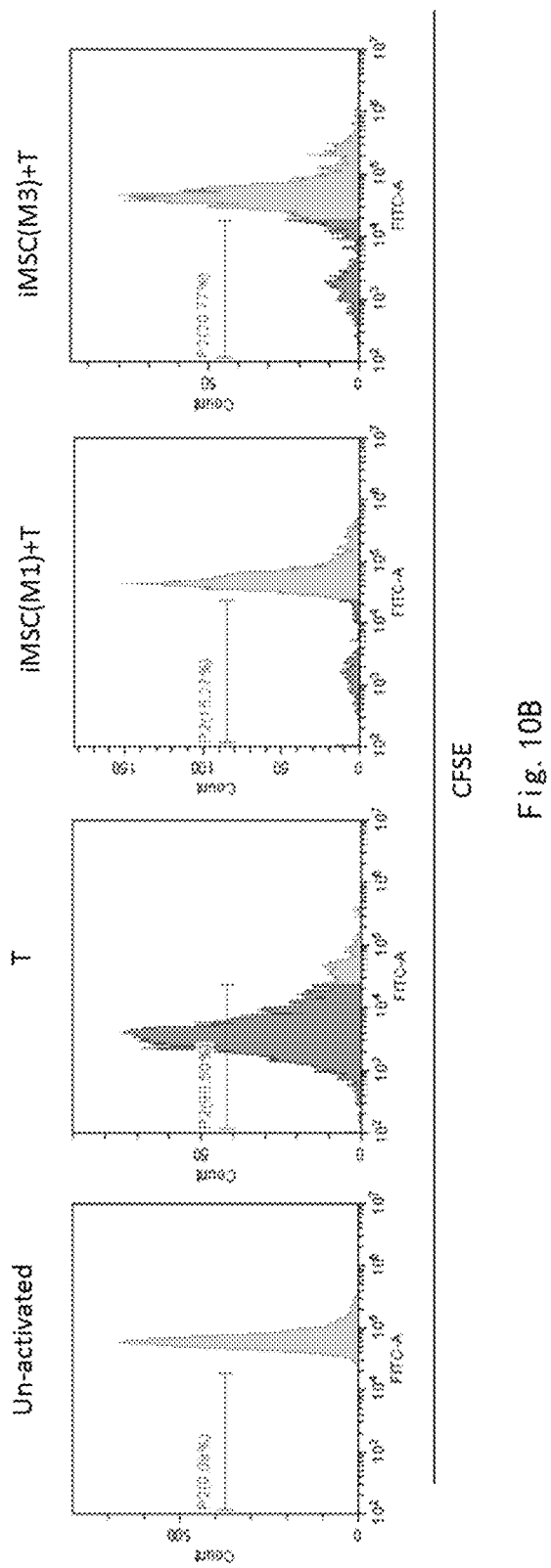

CFSE-based T cell proliferation assay was carried out according to the protocol as described in Example 4 to evaluate the immunosuppressive effect of the above iMSCs (FIG. 10B).

It was found that the iMSCs of P3 cultured in M3 (3% HPLT) medium maintained MSC characteristics, including tri-lineage differentiation (FIG. 10A) and immunosuppressive effect (FIG. 10B).

The above examples 6-10 demonstrated that, although M3 medium containing HPLT could support iMSC expansion, it couldn't stably maintain the stem cell phenotype (CD90 expression) of iMSCs during the prolonged expansion due to lack of ethanolamine and putrescine 2HCl, while M4 medium containing all of HPLT, ethanolamine and putrescine 2HCl could more stably maintain the stem cell phenotype (CD90 expression) of iMSCs during the prolonged expansion. This demonstrated that ethanolamine and putrescine 2HCl were crucial for stably maintaining the stem cell phenotype (CD90 expression) of iMSCs during the prolonged expansion.

In addition, as compared with M1, M4 avoided the use of the animal-derived components, and could promote robust iMSC proliferation and provide iMSCs with the immunosuppressive effect.

In summary, by combining the results of Examples 6-10, M4 was found to support the prolonged expansion of iMSCs without losing iMSC characteristics (including morphology, phenotype, differentiation potential and immunomodulatory effect), indicating the high potential of M4 in clinical applications.

By combining the examples 1-4 with the examples 6-10, ethanolamine, putrescine 2HCl and HPLT were found to synergistically support the prolonged expansion of iMSCs.

Examples 11-13

The present examples were carried out in order to demonstrate that FGF2, HSA and/or Heparin sodium could further promote the iMSC expansion.

Example 11

As an example, M3 medium with 5% HPLT was used in order to verify the effect of FGF2 on the iMSC expansion. Cryopreserved iMSCs (RC01005, Nuwacell Co., Ltd.) were seeded in 6-well plates at 50000 cells/well in M1 medium to thaw the cells. The medium was replaced 24 h later with 2 ml/well of the following medium: M1; or M3 (with 5% HPLT) further supplemented with or without different concentration of FGF2 (Nuwacell Co., Ltd.). M1 medium had the composition as described in the Example 7. M3 (5% HPLT) had the same composition as that in the example 7. On day 4 of culture, when cells got confluent, the cell number of iMSCs was counted by cell viability analyzer (Vi-CELLTMXR, BECKMAN COULTER) according to the protocol as described in Example 2.

Figure 11:
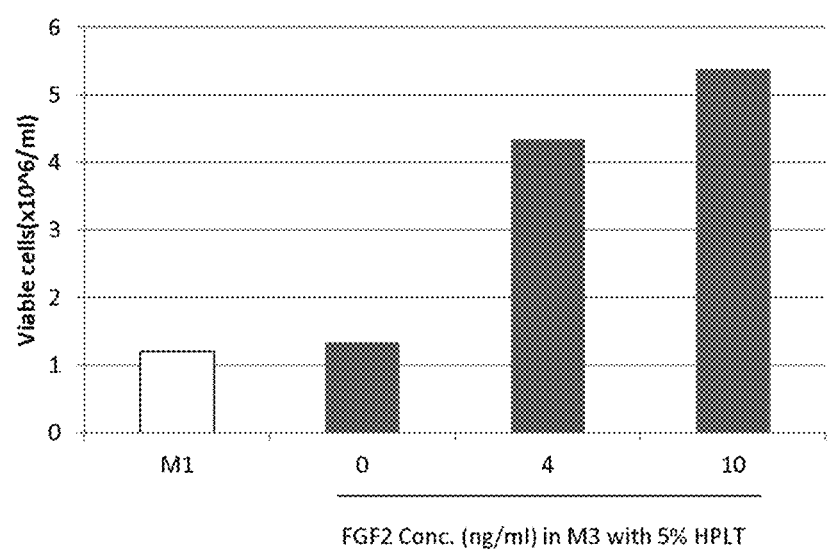
FIG. 11 shows the effect of different media, M1, M3, and M3 further supplemented with different concentrations of FGF2, on the proliferation of iMSCs according to Example 11.

As shown in FIG. 11, the cell number of the iMSCs expanded in M3 (5% HPLT) further supplemented with FGF2 was significantly higher than that of the iMSCs expanded in M3 (5% HPLT) without FGF2 (the former was about 3.1 or about 3.9 times the latter). Similar to the results in FIG. 5, FGF2 was also found to significantly promote iMSC expansion (FIG. 11).

Example 12

In view that HPLT is highly priced and limited in supply, HSA (Chengdu Rongsheng Pharmaceuticals Co., Ltd., China) was added to reduce the amount of HPLT. As an example, M3 medium with low concentration of HPLT (e.g., 0.5% HPLT) was used in order to verify the effect of HSA on the iMSC expansion. Cryopreserved iMSCs (RC01005, Nuwacell Co., Ltd.) were seeded in 6-well plates at 1000 cells/well in M1 medium to thaw the cells. M1 medium had the composition as described in the Example 6. The medium was replaced 24 h later with 2 ml/well of the following medium: M3 (0.5% HPLT) further supplemented with or without 4 mg/L untreated HSA (w/o dialysis) or dialyzed HSA. M3 (0.5% HPLT) had the same composition as M3 in the example 7 except for the concentration of HPLT. HSA dialysis was carried out by placing HSA into a dialysis bag and placing the dialysis bag in DPBS (C14190500BT, Gibco) solution at 4° C. overnight, wherein the ratio of HSA to DPBS was 1:50 (v:v) and the pore size of the bags was 15 KD. The medium was changed with the same medium every three days. The cell morphology of day 10 culture was shown in FIG. 12A and the cell number was counted by cell viability analyzer (Vi-CELLTMXR, BECKMAN COULTER) according to the protocol as described in Example 5 (FIG. 12B).

Figure 12A:
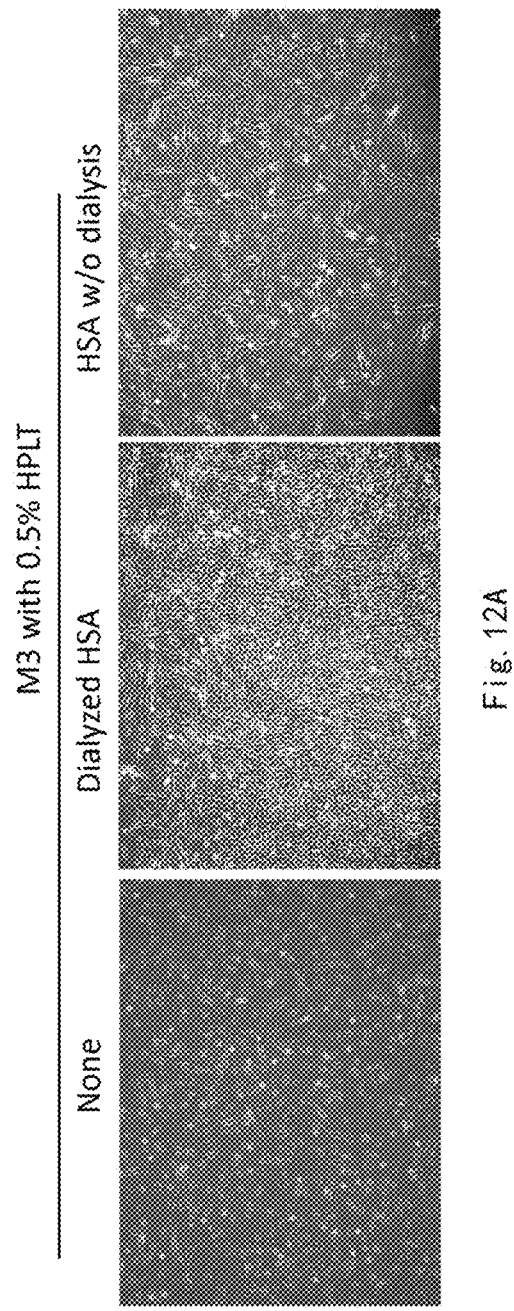
Figure 12B:
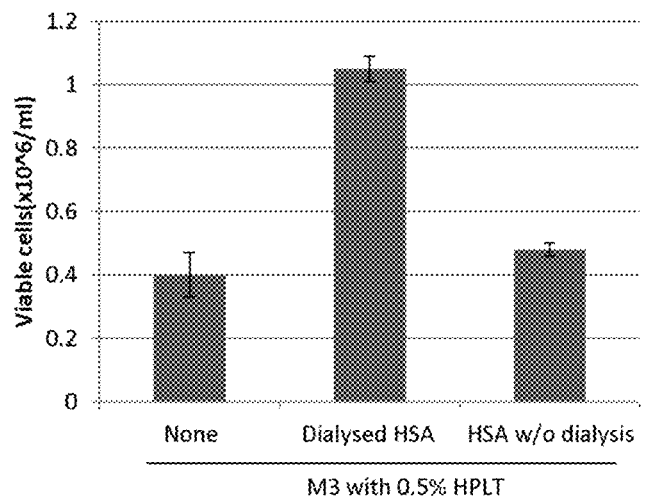

As shown in FIG. 12A, compared with the iMSC cells cultured in M3 (0.5% HPLT) without HSA, the iMSC cells cultured in M3 (0.5% HPLT) with untreated or dialyzed HSA were found to expand and could maintain their original morphological characteristics (like spindle shaped fibroblasts). In particular, the iMSC cells cultured in M3 (0.5% HPLT) with dialyzed HSA grew much better. In addition, the effect of HSA and in particular dialyzed HSA for promoting the expansion of the iMSC cells was also demonstrated by the results of cell number analysis (FIG. 12B). As shown in FIG. 12B, the cell number of the iMSCs expanded in M3 (0.5% HPLT) with dialysed HSA was about 2.3 times that of the iMSCs expanded in M3 (0.5% HPLT) with untreated HSA (w/o dialysis).

Example 13

As an example, M3 medium with HPLT was used in order to further verify the effects of dialyzed HSA and Heparin sodium on the iMSC expansion. Cryopreserved iMSCs (RC01005, Nuwacell Co., Ltd.) were seeded in 6-well plates at 1000 cells/well in M1 to thaw the cells. M1 medium had the composition as described in the Example 6. The media was replaced 24 h later with 2 ml/well of the following medium: M1; or M3 having different concentrations of HPLT and further supplemented with 4 mg/L dialyzed HSA or with 4 mg/L dialyzed HSA and 25 μg/ml Heparin sodium (Cat. No.: A16198, Thermo fisher). The medium was changed with the same medium every three days. The cell number of day 10 culture was counted by cell viability analyzer (Vi-CELLTMXR, BECKMAN COULTER) according to the protocol as described in Example 5. The results were shown in FIG. 13.

Figure 13:
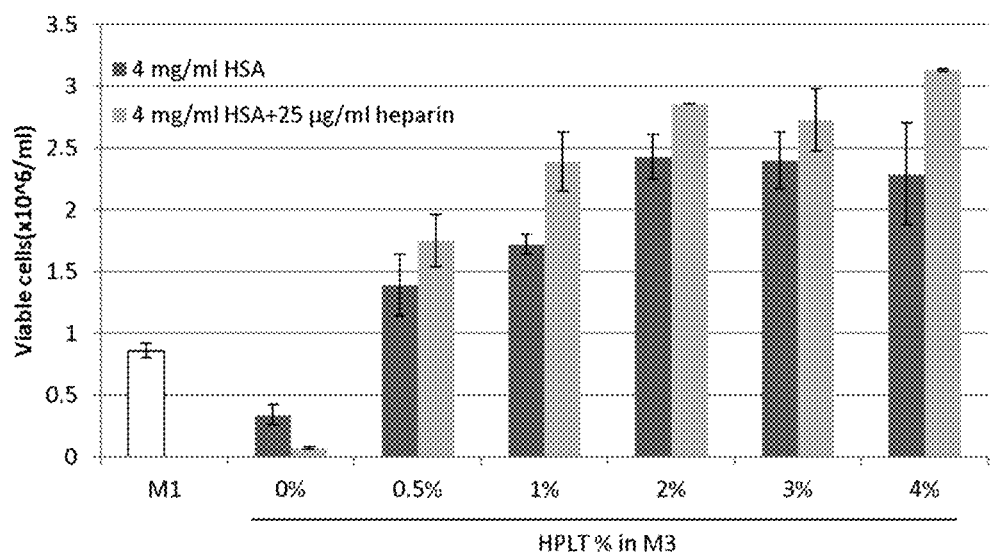
FIG. 13 shows the effects of dialyzed HSA and heparin sodium in M3 with different concentrations of HPLT on the proliferation of iMSCs according to Example 13.

As confirmed by comparing the results of FIG. 13 with the results (iMSC histogram) of FIG. 7, the addition of dialyzed HSA could significantly lower the required HPLT concentration in promoting iMSC growth. In addition, FIG. 13 demonstrated that heparin sodium could further promote iMSC growth.

In summary, the examples 11-13 demonstrated that the addition of HSA (in particular, dialyzed HSA), FGF2 and/or Heparin sodium could further promote the iMSC expansion, and the addition of dialyzed HSA could significantly lower the HPLT concentration required in promoting iMSC growth.

Examples 14-17

The present examples were carried out to further develop a serum-free and xeno-free MSC expansion medium, M5, in order to more persistently support the prolonged expansion of iMSCs.

Example 14

Cryopreserved iMSCs (RC01005, Nuwacell Co., Ltd.) were seeded in 6-well plates at 1000 cells/well in M1 medium to thaw the cells. M1 medium had the composition as described in the Example 1. The medium was replaced 24 h later with 2 ml/well of M5 medium containing no HPLT or M5 medium containing different concentrations of HPLT (0.50%, 1%, 2% or 3% by volume). M5 medium contained IMDM+DMEM/F12 (50%/50%), 1% by volume of Glutamax, 1-150 μg/ml (e.g., 120 μg/ml) of transferrin, 5 μg/ml of insulin, 1-150 μg/ml (e.g., 110 μg/ml) of Mg Ascorbate, 20 μM of Ethanolamine, 10 μM of Putrescine 2HCl, indicated concentrations (0%, 0.5%, 1%, 2% and 3% by volume) of HPLT, 4 ng/ml of FGF2, 1 μM of Hydrocortisone, 14 ng/ml of $Na_2SeO_3$, 0.11 mg/ml of Sodium pyruvate, 2 mg/ml of HSA, 50 μM of MTG, 0.5-20 mM (e.g., 20 mM) of nicotinamide and 50 μg/ml of heparin sodium. iMSCs were cultured in the above medium for 10 days and the medium was changed with the same medium every three days. The cell number of cells was counted by cell viability analyzer (Vi-CELLTMXR, BECKMAN COULTER) according to the protocol as described in Example 5.

Figure 14:
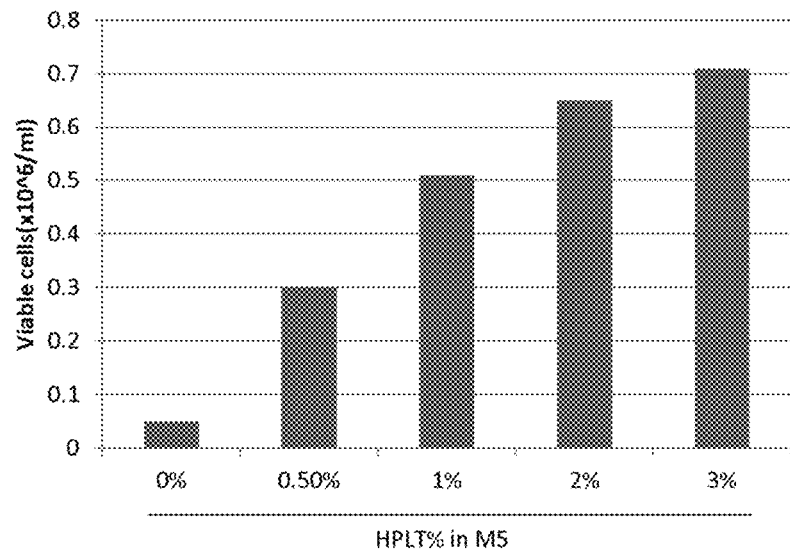
FIG. 14 shows the effect of different concentrations of HPLT in M5 on the proliferation of iMSCs according to Example 14.

As shown in FIG. 14, similar to M2, the cell number of the iMSCs cells cultured in M5 containing HPLT was significantly higher than that of the iMSC cells cultured in M5 containing no HPLT (the former was about 6, 10, 13 or 14 times the latter). Similarly, HPLT in M5 was found to promote iMSC proliferation.

Example 15

Figure 15A:
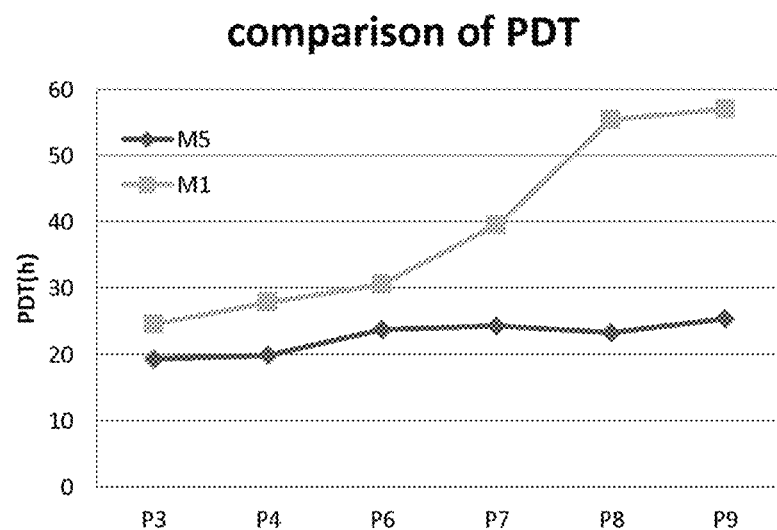

Cryopreserved iMSCs (RC01005, Nuwacell Co., Ltd.) were seeded in 6-well plates at 50000 cells/well in M1 medium to thaw the cells. The medium was replaced 24 h later with 2 ml/well of the following medium: M1, M4 or M5. M1 medium had the composition as described in the Example 14 and was used as a control. M4 medium had the composition as described in the Example 8. M5 medium had the composition as described in the Example 14. iMSCs were cultured and passaged in indicated medium until passage 9. On day 4 of culture for each passage, when cells got confluent, the cell number was counted by cell viability analyzer (Vi-CELLTMXR, BECKMAN COULTER) according to the protocol as described in Example 2 (FIG. 15A). The cell morphology of passage 8 was shown in FIG. 15B.

Figure 15B:
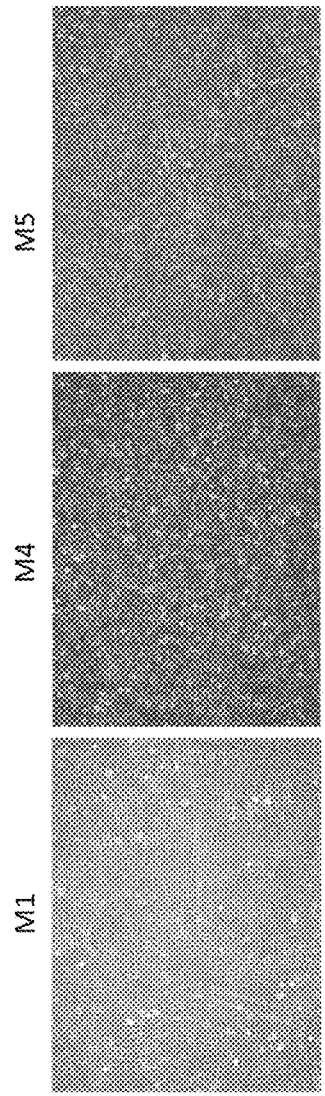

At high passage number (P8), the iMSCs cultured in M4 and M5 maintained better MSC original morphological characteristics (like spindle shaped fibroblasts), while the iMSCs cultured in M1 couldn't (the cells became larger and irregular) (FIG. 15B). The iMSCs expanded in M5 had lower PDT (Population Doubling Time), which was substantially stably maintained at about 20-24 hrs for all passages throughout the prolonged expansion while the iMSCs cultured in M1 had higher PDT, which was significantly increased from P3 (about 25 hrs) to P9 (about 57 hrs) throughout the prolonged expansion (FIG. 15A). The lower PDT at each passage meant a higher expansion efficiency at each passage, and similar PDT at each passage meant that the expansion capability of cells at each passage could be better maintained. Accordingly, compared with M1 medium, M5 medium consistently supported robust iMSC growth throughout the prolonged expansion.

Example 16

Cryopreserved iMSCs (RC01005, Nuwacell Co., Ltd.) were seeded in 6-well plates at 50000 cells/well in M1 medium to thaw the cells. The medium was replaced 24 h later with 2 ml/well of the following medium: M1, M4 or M5. M1, M4 and M5 media had the composition as described in the Example 15. iMSCs (RC01005, Nuwacell Co., Ltd.) cultured in M1, M4 or M5 were harvested at passage 1, 4 and 7. The cells were stained with CD90-FITC antibody (BD Pharminge, 555595), and the percentage of $CD90^+$ cells was detected by flow cytometry according to the protocol as described in Example 3 (FIG. 16).

Figure 16:
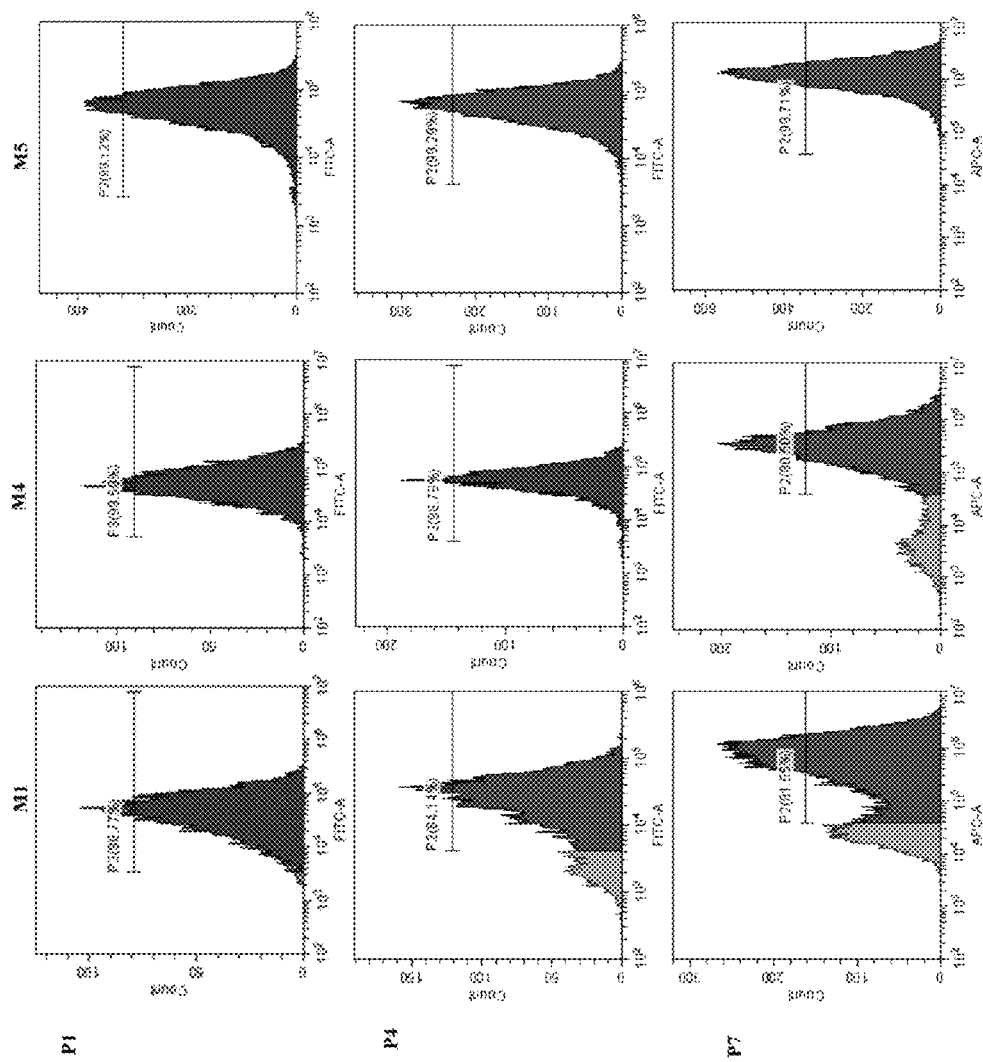
FIG. 16 shows the effect of different media, M1, M4 and M5, on the CD90 expression of iMSCs during the prolonged expansion according to Example 16.

As shown in FIG. 16, in case where iMSCs were cultured using M1, CD90-expressing cells were quickly reduced from 98.77% of P1 to 84.14% of P4 and then to 81.55% of P7, which showed that M1 could not stably maintain the stem cell phenotype of iMSCs from P1 to P7 during the prolonged expansion of the iMSCs. In case where iMSCs were cultured using M4, the CD90 expression was stably maintained from passage 1 to passage 4 (from 99.59% to 98.78% for CD90-expressing cells), and until Passage 7, the percentage of $CD90^+$ cells was dropped. In contrast, M5 more stably maintained CD90 expression up to passage 7 compared to M1 and M4.

Example 17 iMSCs (RC01005, Nuwacell Co., Ltd.) were cultured in M5 for 4 passages and tested for their tri-lineage differentiation potential according to the protocol described in Example 10. Further, iMSCs (RC01005, Nuwacell Co., Ltd.) were cultured in M1 or M5 for 4 passages and tested for their immunosuppressive effect according to the protocol described in Example 4. M1 and M5 media had the composition as described in the Example 15.

Figure 17A:
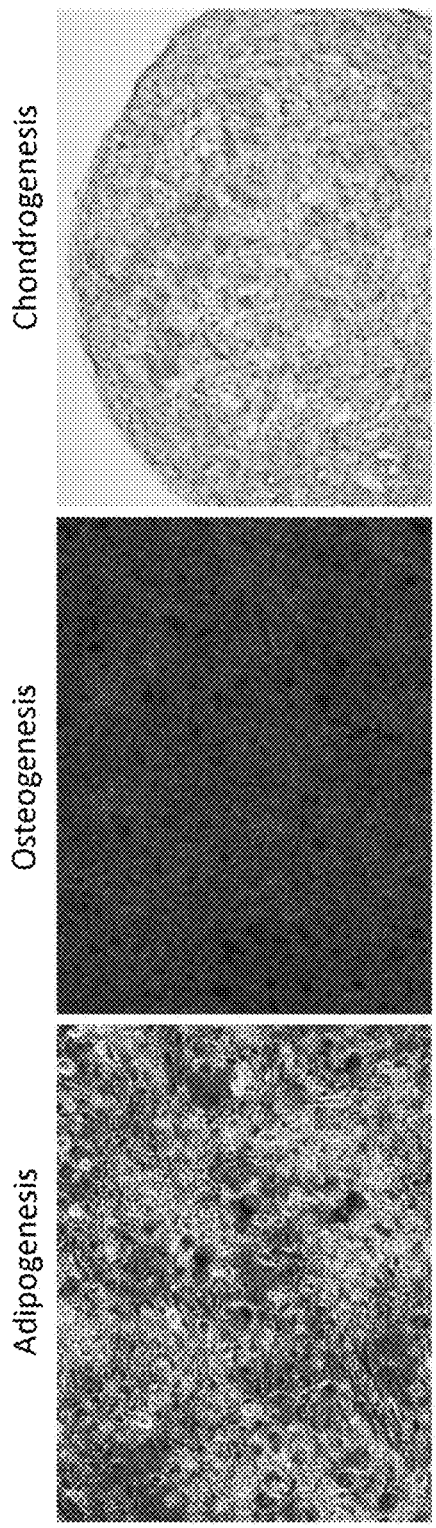
FIGS. 17A-17B shows the results of the tri-lineage differentiation and the CFSE-based T cell proliferation assay of expanded iMSCs according to Example 17, wherein FIG.
Figure 17B:
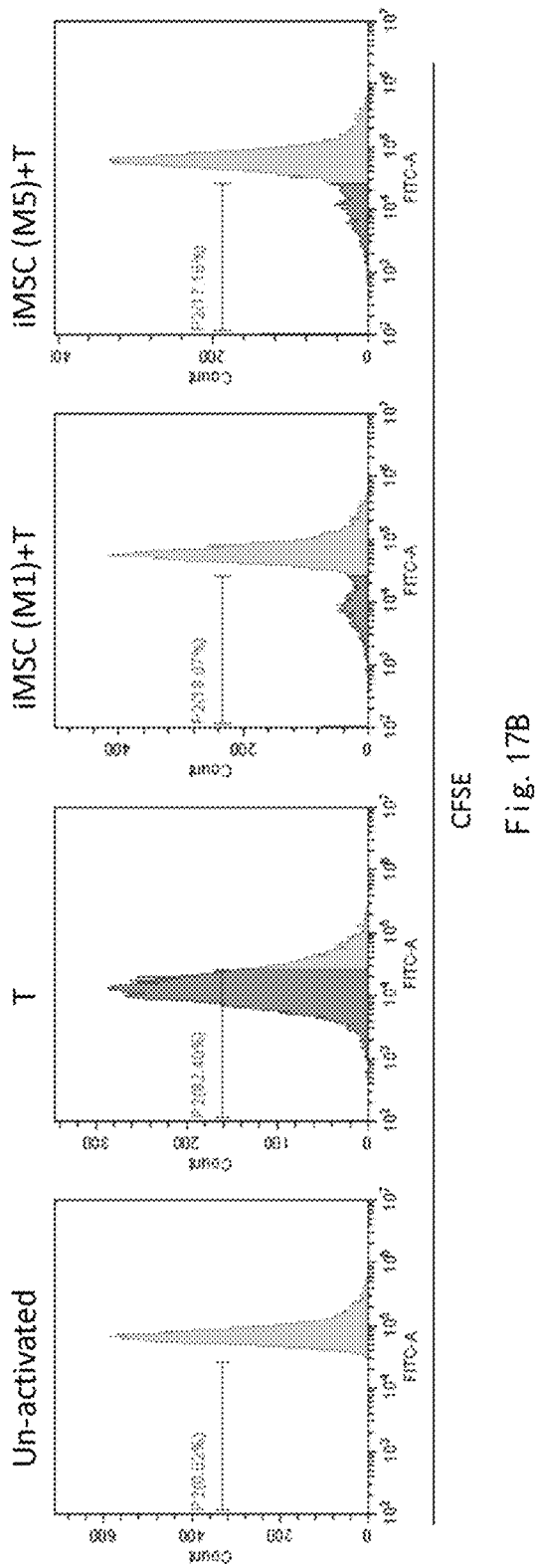

Similar to M1, the iMSCs of P3 cultured in M5 retained MSC characteristics including tri-lineage differentiation (FIG. 17A) and immunosuppressive effect (FIG. 17B).

The above examples 14-17 demonstrated that, during the prolonged expansion of iMSCs, M4 maintained the stem cell phenotype of iMSCs better than M1, and M5 more persistently maintained the stem cell phenotype of iMSCs compared to M4.

In addition, as compared with M1, M5 avoided the use of the animal-derived components, and could promote robust iMSC proliferation and provide iMSCs with the comparable immunosuppressive effect.

In summary, by combining the results of Examples 14-17, M5 was found to more persistently support the prolonged expansion of iMSCs without losing MSC characteristics (including morphology, phenotype, differentiation potential and immunomodulatory effect), indicating the higher potential of M5 in clinical applications.

One skilled in the art would readily appreciate that the methods, compositions, and products described herein are representative of exemplary embodiments, and not intended as limitations on the scope of this disclosure. It will be readily apparent to one skilled in the art that varying substitutions and modifications may be made to the present disclosure disclosed herein without departing from the scope and spirit of this disclosure.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure is not to be limited in terms of the particular embodiments described in this application, which are intended as single illustrations of individual aspects of the disclosure. Many modifications and variations of the disclosure can be made without departing from its spirit and scope, as will be apparent to those skilled in the art. Functionally equivalent media and kits within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

What is claimed is:

1. A culture medium, comprising
   (a) a basal medium;
   (b) 5 to 30 µM of an ethanolamine-based compound;
   (c) 1 to 20 µM of a putrescine-based compound; and
   (d) 0.1% to 10% by volume of a human platelet lysate (HPLT);
   wherein the culture medium is serum-free and xeno-free.

2. The culture medium of claim 1, wherein the ethanolamine-based compound comprises ethanolamine, and the putrescine-based compound comprises putrescine dihydrochloride.

3. The culture medium of claim 1, further comprising a transferrin.

4. The culture medium of claim 3, wherein the transferrin is present in the culture medium at a concentration of 1 to 200 µg/ml.

5. The culture medium of claim 1, further comprising an insulin-based compound.

6. The culture medium of claim 5, wherein the insulin-based compound is present in the culture medium at a concentration of 1 to 15 µg/ml.

7. The culture medium of claim 1, further comprising an antioxidant.

8. The culture medium of claim 7, wherein the antioxidant is present in the culture medium at a concentration of 1 µg/mL to 200 µg/mL.

9. The culture medium of claim 1, further comprising glutamine or a derivative thereof.

10. The culture medium of claim 9, wherein the glutamine or the derivative thereof is present in the culture medium at a concentration of 0.1% to 5% by volume.

11. The culture medium of claim 1, comprising 5 to 30 µM of ethanolamine, 1 to 20 µM of putrescine dihydrochloride, 0.1% to 10% by volume of HPLT, 1 to 150 µg/ml of transferrin, 1 to 10 µg/ml of insulin, 1 to 150 µg/ml of ascorbate, and 0.5% to 5% by volume of glutamine in the basal medium.

12. The culture medium of claim 1, further comprising a growth factor.

13. The culture medium of claim 12, wherein the growth factor is selected from the group consisting of EGF, IGF, VEGF, PDGF, FGF2, TGFβ and any combination thereof.

14. The culture medium of claim 12, wherein the growth factor is present in the culture medium at a concentration of 1 to 20 ng/ml.

15. The culture medium of claim 1, further comprising a corticoid compound.

16. The culture medium of claim 15, wherein the corticoid compound is selected from the group consisting of hydrocortisone, corticosterone, dehydrocorticosterone, cortisone, and any combination thereof.

17. The culture medium of claim 15, wherein the corticoid compound is present in the culture medium at a concentration of 0.1 to 5 µM.

18. The culture medium of claim 1, further comprising a human serum albumin (HSA).

19. The culture medium of claim 18, wherein the HSA comprises dialyzed HSA.

20. The culture medium of claim 18, wherein the HSA is present in the culture medium at a concentration of 1 to 20 mg/ml.

21. The culture medium of claim 1, further comprising a heparin-based compound.

22. The culture medium of claim 21, wherein the heparin-based compound is present in the culture medium at a concentration of 1 to 150 µg/ml.

23. The culture medium of claim 11, further comprising 1 to 15 ng/ml of FGF2, 0.5 to 5 µM of hydrocortisone, 1 to 10 µM of lipoic acid, 1 to 30 µM of $FeSO_4$, and 0.1 to 10 µM of $Fe(NO_3)_3$ in the basal medium.

24. The culture medium of claim 11, further comprising 1 to 15 ng/ml of FGF2, 0.5 to 5 µM of hydrocortisone, 5 to 20 ng/ml of $Na_2SeO_3$, 0.05 to 5 mg/ml of sodium pyruvate, 1 to 10 mg/ml of HSA, 10 to 150 µM of MTG, 0.5 to 20 mM of nicotinamide (NAM), and 10 to 100 µg/ml of heparin sodium in the basal medium.

25. The culture medium of claim 1, comprising 10 to 30 µM of ethanolamine, 1 to 15 µM of putrescine dihydrochloride, and 0.5% to 5% by volume of HPLT in the basal medium.

26. A method for expanding mesenchymal stem cells (MSCs), comprising contacting the MSCs with the culture medium of claim 1.

27. The method of claim 26, wherein the MSCs are continuously expanded for multiple passages.

28. The method of claim 27, wherein the MSCs are continuously expanded for at least 4 passages.

29. The method of claim 27, wherein the MSCs are continuously expanded for at least 7 passages.

30. The method of claim 27, wherein the MSCs are continuously expanded for at least 9 passages.

* * * * *